(12) United States Patent
Mougin

(10) Patent No.: US 7,959,906 B2
(45) Date of Patent: *Jun. 14, 2011

(54) HAIR-COSMETIC COMPOSITION COMPRISING AT LEAST ONE FILM-FORMING GRADIENT COPOLYMER, AEROSOL COMPOSITION COMPRISING THE COSMETIC COMPOSITION AND METHOD FOR TREATING HAIR USING THE COMPOSITION

(75) Inventor: Nathalie Mougin, Paris (FR)

(73) Assignee: L'ORéal S.A., Paris (FR)

( * ) Notice: Subject to any disclaimer, the term of this patent is extended or adjusted under 35 U.S.C. 154(b) by 1309 days.

This patent is subject to a terminal disclaimer.

(21) Appl. No.: 10/734,181

(22) Filed: Dec. 15, 2003

(65) Prior Publication Data

US 2004/0180019 A1 Sep. 16, 2004

Related U.S. Application Data

(60) Provisional application No. 60/459,259, filed on Apr. 2, 2003.

(30) Foreign Application Priority Data

Dec. 13, 2002 (FR) .................................... 02 15855
Mar. 21, 2003 (FR) .................................... 03 03506

(51) Int. Cl.
*A61Q 5/06* (2006.01)
*A61Q 5/00* (2006.01)
(52) U.S. Cl. .................... 424/70.16; 424/47; 424/70.11
(58) Field of Classification Search .................. None
See application file for complete search history.

(56) References Cited

U.S. PATENT DOCUMENTS

| | | | |
|---|---|---|---|
| 3,907,984 A | | 9/1975 | Calvert et al. |
| 5,527,840 A | * | 6/1996 | Chutko et al. ................ 523/412 |
| 5,807,937 A | * | 9/1998 | Matyjaszewski et al. .... 526/135 |
| 6,113,881 A | * | 9/2000 | Bhatt et al. ...................... 424/45 |
| 6,310,165 B1 | | 10/2001 | Wang |
| 6,312,672 B1 | | 11/2001 | Coolbaugh et al. |
| 2002/0019476 A1 | | 2/2002 | Berge et al. |

FOREIGN PATENT DOCUMENTS

GB 1 541 176 2/1979

OTHER PUBLICATIONS

M. Kryszewski, "Gradient Polymers and Copolymers," Polymers for Advanced Technologies, vol. 9, No. 1, Apr. 1, 1998, pp. 244-259.

* cited by examiner

*Primary Examiner* — Jyothsna A Venkat
(74) *Attorney, Agent, or Firm* — Finnegan, Henderson, Farabow, Garrett & Dunner, LLP

(57) ABSTRACT

A hair-cosmetic composition comprising, in a cosmetically acceptable medium, at least one film-forming gradient copolymer comprising at least two different monomeric residues, and displaying a mass polydispersity index (Ip) less than or equal to 2.5, wherein the composition is able to form a film that has a strain at break $\epsilon_r$ ranging from 5% to 2500%, and/or a Young's modulus ranging from 0.5 to 1200 Mpa, and/or an instantaneous elastic recovery $\epsilon_i$ greater than or equal to 10%. An aerosol composition packaged in an aerosol device, comprising a propellant and a haircare composition as defined above, and also a method for treating the hair, such as a styling method, comprising applying the haircare composition or the aerosol composition above to the hair.

31 Claims, 5 Drawing Sheets

10% methacrylic acid initially:

Copolymer with a very low gradient, for which nanostructurization cannot be expected.

20% methacrylic acid initially:

Copolymer with a hydrophilic "head" and hydrophobic "tail", with a gradient that is sufficiently pronounced to lead to nanostructurization.

50% methacrylic acid initially:

Since the monomers are isoreactive in these conditions, the copolymer obtained is of the alternating type.

FIG. 2

HAIR-COSMETIC COMPOSITION COMPRISING AT LEAST ONE FILM-FORMING GRADIENT COPOLYMER, AEROSOL COMPOSITION COMPRISING THE COSMETIC COMPOSITION AND METHOD FOR TREATING HAIR USING THE COMPOSITION

This application claims benefit of U.S. Provisional Application No. 60/459,259, filed Apr. 2, 2003.

This disclosure relates to novel hair-cosmetic compositions comprising at least one film-forming gradient copolymer comprising at least two monomeric residues, such as amphiphilic gradient copolymers, that may, for example, be soluble or dispersible in water and/or in organic solvents, and wherein the at least one film-forming copolymer exhibits a mass polydispersity index (Ip) less than or equal to 2.5, wherein the composition is able to form a film comprising at least one of the characteristics defined herein.

Styling compositions packaged in the form of an aerosol spray generally comprise a high proportion of alcohol. Following the recent sensitization of public opinion to environmental problems resulting from the emission of volatile organic products into the atmosphere, cosmetics with a high alcohol content are currently under scrutiny.

One solution for reducing the amount of alcohol, or even eliminating alcohol from the formulations completely, is replacing it with an equivalent amount of water. However, adding large amounts of water to aerosol sprays intended for fixation of hair, such as lacquers, can lead to an undesirable distortion of the hair and to a degradation of the formulation's cosmetic properties. Moreover, most propellants of the hydrocarbon type are incompatible with water and for this reason it is generally not possible to use them in compositions with a high water content.

Conventional radical polymers, i.e. those obtained by classic radical polymerization, can also be used to reduce or replace a formulation's alcohol content, in solution in ethanol, in water, or in a water/ethanol mixture.

Even so, many polymers currently used are not very compatible with water, and may precipitate. In fact, even if they comprise hydrophilic units, these polymers can also have the drawback of possessing considerable polydispersity of composition, meaning that some polymer chains include the hydrophilic units necessary for solubility, whereas others do not have these units and are therefore insoluble in hydrophilic media. As a result, there are problems of demixing within the composition.

This disclosure overcomes at least one drawback of the prior art by proposing, as recited in the claims herein, a hair-cosmetic composition comprising at least one film-forming polymer of the type that avoids the problems of demixing within the formulation, while providing the desired cosmetic properties.

One aspect of the present disclosure is a hair-cosmetic composition comprising, in a cosmetically acceptable medium, at least one film-forming gradient copolymer comprising at least two different monomeric residues, and displaying a mass polydispersity index (Ip) less than or equal to 2.5, for example, ranging from 1.1 to 2.3, or for further example, from 1.15 to 2.0, and even further for example, ranging from 1.2 to 1.9 or 1.8, wherein the composition is able to form a film comprising at least one of the following characteristics:

a strain at break $\epsilon_r$ ranging from 5% to 2500%, for example, from 10% to 2000%, and further for example, from 15% to 1000%, a Young's modulus ranging from 0.5 to 1200 MPa, for example, from 1 to 1000 MPa, further for example, from 2 to 800 MPa, and an instantaneous elastic recovery $\epsilon_i$ greater than or equal to 10%, for example greater than or equal to 25%, and further, for example, greater than or equal to 35%, and ranging, for example, from 10 to 100%, for instance, from 25% to 98%, or for further example, from 35% to 95%.

Another aspect of the present disclosure is an aerosol composition packaged in an aerosol device comprising a propellant and a haircare composition as defined herein.

Also, disclosed herein, is a method of treatment of hair, such as a method of styling, comprising the application of a haircare composition, as disclosed herein, to the hair and/or spraying the hair with an aerosol composition, and if necessary, leaving the hair thus treated to dry.

BRIEF DESCRIPTION OF THE DRAWINGS

FIG. 2 shows three styrene/methacrylic acid gradient copolymers obtained using different amounts of starting monomers, with the white units corresponding to styrene units and the dark units corresponding to methacrylic acid units.

Figure 1:
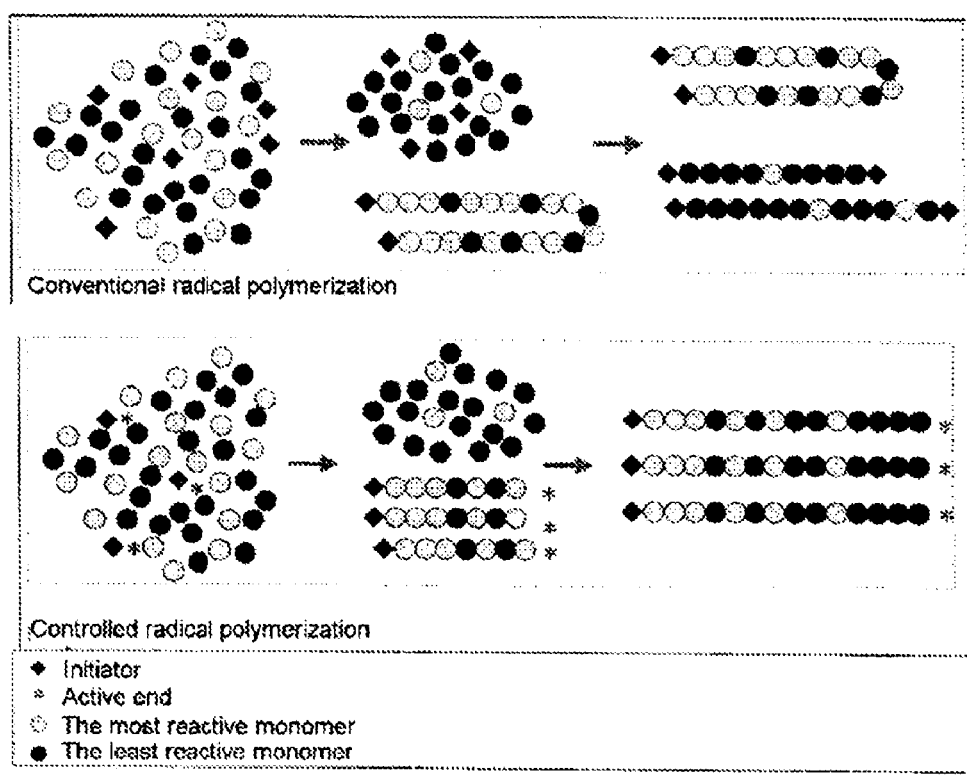
FIG. 1 shows the differing polymer morphology that results from a conventional radical polymerization process as compared to that resulting from a controlled radical polymerization process.

Gradient copolymers, as disclosed herein, can have a low dispersity in composition and the polymer chains comprising the gradient copolymers can have similar or the same structures. Therefore, such gradient copolymers are compatible with one another and, as a result, cosmetic compositions comprising these copolymers can exhibit less than all of the drawbacks and limitations of the compositions of the prior art.

The at least one film-forming gradient copolymer, as disclosed herein, can, for example, be easily manipulated in water or in an organic solvent medium, while retaining its useful rheological properties.

Furthermore, the at least one film-forming gradient copolymer can comprise a sufficient amount of hydrophilic monomeric residue, making it more readily soluble. Without being bound by theory, it is believed that solubility is promoted when all the polymer chains have the same composition.

The at least one copolymer disclosed herein, can be chosen from film-forming gradient copolymers, which comprise at least two different monomeric residues, and which have a low mass polydispersity as defined herein, and for instance, a low composition polydispersity.

The mass polydispersity can be illustrated using the mass polydispersity index (Ip) of the copolymer, which is equal to the ratio of the weight-average molecular weight (Mw) to the number-average molecular weight (Mn).

A low mass dispersity as defined herein reflects approximately identical chain lengths, which is the case for the film-forming gradient copolymers as disclosed herein.

According to the disclosure, the at least one film-forming gradient copolymer has a mass polydispersity index less than or equal to 2.5, for example, ranging from 1.1 to 2.3, for instance, ranging from 1.15 to 2.0, or further, for example, from 1.2 to 1.9.

Furthermore, the weight-average molecular weight of the at least one film-forming gradient copolymer, can be ranging from 5,000 g/mol to 1,000,000 g/mol, for instance, ranging from 5,500 g/mol to 800,000 g/mol, and for further example, ranging from 6,000 g/mol to 500,000 g/mol.

The number-average molecular weight of the at least one film-forming gradient copolymer can also range from 5,000 g/mol to 1,000,000 g/mol, for instance, ranging from 5,500 g/mol to 800,000 g/mol, and further for example, ranging from 6,000 g/mol to 500,000 g/mol.

The weight-average (Mw) and number-average (Mn) molecular weights are determined by gel permeation liquid chromatography ("GPC") (wherein eluent THF, a calibration curve established with linear polystyrene standards, and a refractometric detector are used).

The at least one film-forming gradient copolymer, according to the present disclosure, could, for example, have a low composition dispersity. For the purposes of this disclosure, low composition dispersity means that all the polymer chains of the at least one copolymer have a roughly similar composition (i.e. a concatenation of monomers) and are therefore almost homogeneous in composition.

In order to show that all the polymer chains of the at least one film-forming gradient copolymer have a similar composition, liquid adsorption chromatography ("LAC") can be used to separate the chains of the copolymers according to their polarity, rather than according to their molecular weight. Without being bound by theory, it is believed that the chains' polarity reflects the chemical composition of the polymers of which the material is constituted.

One may refer to the publication Macromolecules (2001), 34, 2667, which describes the LAC technique.

For example, the composition polydispersity can be defined from the LAC curve (the curve representing the proportion of polymers as a function of the elution volume): if we call the minimum value of the elution volume at mid-height of the curve $V^{1/2}$min, and the maximum value of the elution volume at mid-height of the curve $V^{1/2}$max, the composition polydispersity is regarded as low if the difference ($V^{1/2}$max−$V^{1/2}$min) is less than or equal to 3.5, or, for example, ranging from 1 to 2.8 and for further example, ranging from 1.2 to 2.5.

The LAC curve can be further defined by a Gaussian curve with the formula:

$$y = \frac{A}{w\sqrt{\frac{\pi}{2}}} \times e^{-2\frac{(x-x_0)^2}{w^2}} + y_o$$

wherein:
$x_0$ is the value of x (elution volume) at the centre of the peak
w is equal to twice the standard deviation of the Gaussian distribution (i.e. 2σ) or corresponds approximately to 0.849 times the width of the peak at mid-height
A is equal to the area under the peak
$y_0$ is the value of y corresponding to $x_0$.
The composition dispersity can also be defined by the value of w as defined above. For example, the composition dispersity can be wherein w ranges from 1 to 3, or ranges, for example, from 1.1 to 2.3 and further ranges, for example, from 1.1 to 2.0.

The at least one film-forming gradient copolymer, according to the present disclosure, can be obtained by living or pseudo-living polymerization. It is known that living polymerization is a polymerization for which the growth of the polymer chains only ceases with the disappearance of the monomer. The number-average molecular weight (Mn) increases with the degree of conversion. Anionic polymerization is a typical example of living polymerization. Such polymerizations result in copolymers with low mass dispersity, i.e. polymers with a mass polydispersity index (Ip) generally less than 2.

As for pseudo-living polymerization, it is associated with controlled radical polymerization. Among the main types of controlled radical polymerization, non-limiting mention may be made of:

radical polymerization controlled by nitroxides. Reference may be made, for example, to Patent Applications Nos. WO 96/24620 and WO 00/71501, which describe the tools for this polymerization and their use, as well as to the articles published by Fischer (Chemical Reviews, 2001, 101, 3581), by Tordo and Gnanou (J. Am. Chem. Soc. 2000, 122, 5929) and Hawker (J. Am. Chem. Soc. 1999, 121, 3904);

atom transfer radical polymerization, for instance, as described in patent application No. WO 96/30421, which takes place by reversible insertion on an organometallic complex in a carbon-halogen bond; and radical polymerization controlled by sulphur derivatives of the xanthate type, dithioesters, trithiocarbonates or carbamates, as described in Patent Applications Nos. FR 2821620, WO 98/01478, WO 99/35177, WO 98/58974, WO 99/31144, WO 97/01478 and in the article by Rizzardo et al. (Macromolecules, 1998, 31, 5559).

Controlled radical polymerization denotes polymerizations for which the secondary reactions that usually lead to the disappearance of the propagating species (termination or transfer reaction) are made to become very unlikely, relative to the propagation reaction, owing to the action of a free radical controlling agent. The drawback of this form of polymerization can be that when the concentrations of free radicals become large in relation to the concentration of monomer, the secondary reactions become determining again and tend to broaden the mass distribution.

In these forms of polymerization, the polymer chains of the gradient copolymers as disclosed herein grow simultaneously and therefore usually incorporate the same ratios of comonomers at any given moment. All the chains, therefore, can have the same or similar structures, which can result in low composition dispersity. These chains also have a low mass polydispersity index.

Gradient copolymers are copolymers wherein the ratio of the various monomers varies along the length of the chain. The distribution in the polymer chains of the comonomers depends on the variation of the relative concentrations of the comonomers during synthesis.

The at least one film-forming gradient copolymer, according to the present disclosure, includes at least two different monomeric residues, whose concentration along the polymer chain changes gradually, in a regular and predictable manner. Accordingly, all the polymer chains have at least one monomer Mi, wherein, regardless of the normalized position x on the polymer chain, the probability of finding this monomer Mi along the length of the chain is not zero.

One of the characteristics by which gradient copolymers can be defined is that at any moment in the polymerization, all the chains are subject to the presence of all of the monomers. Thus, in the reaction medium, the concentration of each monomer is always non-zero, at any given moment in the polymerization. This distinguishes the gradient copolymers as disclosed herein from the usual block polymers, wherein the variation of the monomers along the polymer chain is not regular. For example, for a diblock copolymer AB, within the block A, the concentration of the other monomer B is always zero.

In the case of random polymers, the variation of the monomers along the polymer chain will normally not be gradual, regular and predictable. As shown in FIG. 1, a random polymer obtained by classical radical polymerization of two monomers will differ from a gradient copolymer in the distribution of the monomers, in that a random polymer is normally not identical on all the chains, nor in the length of the chains, which is normally not identical for all the chains.

For a theoretical description of gradient copolymers, reference may be made to the following works:

T. Pakula et al., Macromol. Theory Simul. 5, 987-1006 (1996);
A. Aksimetiev et al., J. of Chem. Physics 111, No. 5;
M. Janco, J. Polym. Sci., Part A: Polym. Chem. (2000), 38(15), 2767-2778;
M. Zaremski et al., Macromolecules (2000), 33(12), 4365-4372;
K. Matyjaszewski et al., J. Phys. Org. Chem. (2000), 13(12), 775-786;
Gray, Polym. Prepr. (Am. Chem. Soc., Div. Polym. Chem.) (2001), 42(2), 337-338;
K. Matyjaszewski, Chem. Rev. (Washington, D.C.) (2001), 101(9), 2921-2990.

Among gradient copolymers, a distinction may be made between natural gradient copolymers and artificial gradient copolymers.

A natural gradient copolymer is a gradient copolymer obtained by batch synthesis from an initial mixture of the comonomers. The distribution of the various monomers in the chain follows a pattern that can be deduced from the relative reactivity and the initial concentrations of the monomers. These copolymers constitute the simplest class of gradient copolymers as it is the initial mixture that determines the final properties of the product.

An artificial gradient copolymer is a gradient copolymer for which the concentration of monomers is varied, by a special measure, during synthesis. In the case of artificial gradient copolymers, there is a shift from one mixture of monomers to another in the chain owing to a sudden, abrupt change of the monomers in the reaction medium (for instance, stripping of the first mixture or addition of at least one new monomer). There may even be a substantial disappearance of at least one of the monomers to the benefit of at least one other monomer.

The gradient is characterized experimentally by measuring the chemical composition of the polymer during polymerization. Measurement is taken, indirectly, by determining the variation in the content of the different monomers at any given moment. This can be done using NMR and UV, for example.

In general, for polymers prepared by living or pseudo-living polymerization, chain length is related linearly to the degree of conversion. By taking a sample of the polymerization solution, at different moments in the polymerization, and then measuring the difference in the content of each monomer, one can arrive at the composition of the gradient.

In a gradient polymer, generally, the compositions of the chains have a narrow distribution. For instance, there is no overlap between the peak of the gradient copolymer and those of the respective homopolymers, which shows that the material obtained in gradient conditions is made up of polymer chains of identical composition. In contrast, in classical random polymerization, different kinds of chains can normally coexist, including those of the respective homopolymers.

It is possible to characterize gradient copolymers by a vector that is characteristic of each copolymer. In fact, since it is assumed that there is an infinite number of polymers characterized by a given chemical composition, it is possible to define a polymer by describing the distribution of the monomers along the chain. This involves a description with several variables. This vector is a point in space of the chemical compositions.

The more precise definition is that G is a vector whose coordinates are the concentrations of the monomers along the polymer chain. These concentrations are defined by the rules of the reactivity coefficients of each monomer, and are therefore related to the concentration of the free monomers during synthesis: from the moment when the monomer is not at zero concentration in the reaction mixture, it is not at zero concentration in the polymer.

It is therefore possible to characterize gradient copolymers by the function $G(x)$, which defines the composition gradient:

$$\vec{G}(x) = \Sigma \overrightarrow{[Mi](x)}$$

wherein:

x denotes a normalized position on the polymer chain, and [Mi](x) is the relative concentration, at the position x, of the monomer Mi, expressed in mol %.

The function $G(x)$ therefore describes the composition of the gradient copolymer locally. Two different copolymers can have an equivalent overall composition but very different local distributions of the monomers, and therefore different gradients.

For example, in the case of a diblock copolymer AB (50/50), function [A] has a value of 1 up to $x=\frac{1}{2}$ and 0 thereafter.

The factors that can determine the gradient include: the relative reactivity coefficients of each monomer (called $r_i$ for the monomer Mi), which mainly depend on the type of synthesis process employed (e.g., homogeneous, dispersed), and the solvents employed, the initial concentrations of each of the monomers, and any additions of monomers in the course of polymerization.

Thus, for example, consider a gradient copolymer of styrene (M1) with a relative reactivity coefficient $r_1=0.418$ and of methacrylic acid (M2), with $r_2=0.6$, in a system of homogeneous polymerization. By varying the initial concentrations of styrene and methacrylic acid, different gradient copolymers can be obtained, each having chains with entirely different structures.

When the initial concentration of methacrylic acid is 10% by weight, one can obtain a copolymer of very low gradient, for which nanostructurization cannot be expected. When the initial concentration is 20% by weight, we obtain a gradient copolymer with a hydrophilic "head" and a hydrophobic "tail," with a gradient that is sufficiently pronounced to lead to nanostructurization. When the concentration is 50% by weight, the monomers can be isoreactive in these conditions, and therefore, the copolymer obtained is of the alternating type.

Although the copolymers described are all gradient copolymers of styrene and methacrylic acid, the difference in the initial concentration of the monomers leads to chains with completely different structures, conferring on the copolymers different properties. FIG. 2 illustrates the influence of the initial monomer compositions on the arrangement of the various monomers along the chain.

In the case of a styrene/methacrylic acid gradient copolymer, the different polymers obtained can be represented as shown in FIG. 2.

The structure of these polymers may be determined by the disappearance of the methacrylic acid as a function of the degree of conversion.

The at least one film-forming gradient copolymer, as disclosed herein, comprises at least two different monomeric residues, wherein each of which can be present in an amount ranging from 1% to 99% by weight, relative to the total weight of the copolymer, such as in an amount ranging from 2% to 98% by weight, relative to the total weight of the copolymer, and for instance, in an amount ranging from 5% to 95% by weight, relative to the total weight of the copolymer.

For example, the at least one film-forming gradient copolymer can comprise at least one monomeric residue resulting from at least one monomer chosen from hydrophilic monomers.

These hydrophilic monomeric residues can be present in an amount ranging from 1% to 99% by weight, relative to the total weight of the copolymer, in an amount ranging, for example, from 2% to 70% by weight, relative to the total weight of the copolymer, in an amount ranging, for example, from 5% to 50% by weight, relative to the total weight of the copolymer, or further, in an amount ranging from 10% to 30% by weight, relative to the total weight of the copolymer.

For the purposes of the present disclosure, "hydrophilic monomer" designates monomers of which the homopolymers are soluble or dispersible in water, or of which an ionic form is soluble or dispersible in water.

A homopolymer is called water-soluble if it forms a clear solution when it is in solution at 1% by weight in water, at 25° C. A homopolymer is called water-dispersible if, at 1% by weight in water, at 25° C., it forms a stable suspension of fine, generally spherical, particles. The average size of the particles making up the dispersion can be less than 1 μm and, more generally, can vary from 5 to 400 nm, and, for example, from 10 to 250 nm. These particle sizes are measured by light scattering.

For example, the hydrophilic monomer can possibly have a Tg less than or equal to 20° C., but more generally can have a Tg greater than or equal to 20° C., such as greater than or equal to 50° C.

The gradient copolymer can also comprise at least one hydrophobic monomeric residue, for example, resulting from a hydrophobic monomer that can be made hydrophilic after polymerization, or a mixture of such monomers. The at least one hydrophobic monomer can be made hydrophilic, for example, by chemical reaction, such as hydrolysis, or by chemical modification of, for example, an ester functional group, by incorporating chains that have a hydrophilic unit, for instance of the carboxylic acid type.

These hydrophobic monomers can be present in an amount ranging from 1% to 99% by weight, relative to the total weight of the copolymer, such as in an amount ranging from 30% to 98% by weight, relative to the total weight of the copolymer, for instance, in an amount ranging from 50% to 95% by weight, relative to the total weight of the copolymer, or such as in an amount ranging from 70% to 90% by weight, relative to the total weight of the copolymer.

For example, the hydrophobic monomers that can be made hydrophilic can be present in an amount ranging from 1% to 99% by weight, relative to the total weight of the copolymer, such as in an amount ranging from 5% to 50% by weight, relative to the total weight of the copolymer, and such as in an amount ranging from 8% to 25% by weight, relative to the total weight of the copolymer.

For example, the hydrophobic monomer may possibly have a Tg less than or equal to 20° C., but more generally can have a Tg greater than or equal to 20° C., such as greater than or equal to 30° C.

For example, the at least one gradient copolymer, as disclosed herein, can comprise at least one monomeric residue resulting from a monomer having a Tg less than or equal to 20° C., such as ranging from −150° C. to 20° C., further ranging from −130° C. to 18° C., and further still ranging from −120° C. to 15° C., or a mixture of such monomers, which may be identical or different.

The monomers with Tg less than or equal to 20° C. can be present in an amount ranging from 1% to 99% by weight, relative to the total weight of the copolymer, such as in an amount ranging from 10% to 90% by weight, relative to the total weight of the copolymer, in an amount ranging from 20% to 80% by weight, relative to the total weight of the copolymer, or for instance, in an amount ranging from 50% to 75% by weight, relative to the total weight of the copolymer.

The monomers with Tg greater than or equal to 20° C. can therefore be present in an amount ranging from 1% to 99% by weight, relative to the total weight of the copolymer, further such as in an amount ranging from 10% to 90% by weight, relative to the total weight of the copolymer, such as in an amount ranging from 20% to 80% by weight, relative to the total weight of the copolymer, for instance, in an amount ranging from 25% to 50% by weight, relative to the total weight of the copolymer.

For the purposes of the present disclosure, "Tg monomer" designates monomers whose homopolymer has such a Tg, measured by the method described hereinbelow.

As disclosed herein, the Tg (or glass transition temperature) is measured in accordance with standard ASTM D3418-97, by differential scanning calorimetry (DSC) in a calorimeter, over a temperature range from −100° C. to +150° C. at a heating rate of 10° C./min in 150-μl aluminium crucibles.

In one aspect of the disclosure, the gradient copolymer of the disclosure comprises three different monomeric residues, wherein each monomeric residue can be present in an amount ranging from 5% to 90% by weight, relative to the total weight of the copolymer, such as in an amount ranging from 7% to 86% by weight, relative to the total weight of the copolymer.

For example, the gradient copolymer can comprise from 5% to 25% by weight of a first monomeric residue, from 5% to 25% by weight of a second monomeric residue and from 50% to 90% by weight of a third monomeric residue.

For further example, the at least one gradient copolymer as disclosed herein, can comprise a hydrophilic monomer ranging from 5% to 25% by weight, relative to the total weight of the copolymer, a monomer with Tg less than or equal to 20° C. in an amount ranging from 50% to 90% by weight, relative to the total weight of the copolymer, and an additional monomer in an amount ranging from 5% to 25% by weight, relative to the total weight of the copolymer.

The hydrophilic monomers, according to the present disclosure, can be chosen from:
  derivatives of $C_1$-$C_6$ aminoalkyl (meth)acrylates, for example N, N-di($C_1$-$C_4$) alkylamino($C_1$-$C_6$)alkyl (meth)acrylates, such as N,N-dimethylaminoethyl methacrylate (MADAME), and N,N-diethylaminoethyl methacrylate (DEAMEA);
  $C_1$-$C_4$ N,N-dialkyl(meth)acrylamides and $C_1$-$C_4$N,N-dialkyl$C_1$-$C_6$aminoalkyl(meth)acrylamides, such as those chosen from N,N-dimethylacrylamide, N,N-dimethylaminopropylacrylamide (DMAPA) and N,N-dimethylaminopropylmethacrylamide (DMAPMA);
$C_1$-$C_8$ dialkyldiallylamines, such as dimethyldiallylamine;
vinylamines;
vinylpyridines, for example 2-vinylpyridine and 4-vinylpyridine;
and the acid salts and quaternized forms thereof.

Among the inorganic acids that may be used, non-limiting mention may be made of sulphuric acid, hydrochloric acid, hydrobromic acid, hydriodic acid, phosphoric acid, and boric acid.

Among the organic acids, that may be used, non-limiting mention may be made of acid comprising at least one group chosen from carboxylic, sulphonic and phosphonic group. The organic acids may be linear, branched, cyclic aliphatic acids, or aromatic acids. The acids can also comprise at least one heteroatom chosen from O and N, for example in the form of hydroxyl groups.

Non-limiting examples of an acid with an alkyl group are acetic acid and propionic acid. A non-limiting example of a polyacid, for instance, is terephthalic acid. Non-limiting examples of hydroxy acid include citric acid and tartaric acid.

Non-limiting examples of quaternizing agents can be chosen from alkyl halides, for instance, methyl bromide, and alkyl sulphates, for instance, methyl sulphate and propane sultone.

With regard to the hydrophilic monomers, non-limiting mention may also be made of:
carboxylic acids, for instance monocarboxylic and dicarboxylic acids, further for instance ethylenic acids, and even further for instance, acrylic acid, methacrylic acid, crotonic acid, itaconic acid, fumaric acid, and maleic acid;
carboxylic anhydrides comprising a vinyl bond, such as maleic anhydride;
ethylenic sulphonic acids, such as styrenesulphonic acid, acrylamidopropanesulphonic acid, and their salts;
vinylbenzoic acid, vinylphosphonic acid, and their salts;
the potassium salts of acryloyloxy-3-sulphopropyl, and the compound of formula $CH_2$=$CHCOOCH_2OCH_2(OH)CH_2SO_3^-Na^+$. 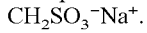

The neutralizing agent may be chosen from inorganic bases, such as LiOH, NaOH, KOH, Ca(OH)$_2$, NH$_4$OH; or may be chosen from organic bases, for example, primary, secondary and tertiary amines, such as alkylamines, optionally hydroxylated, such as dibutylamine, triethylamine, stearamine, and alternatively 1-amino-2-methyl-2-propanol, monoethanolamine, diethanolamine, and stearamidopropyldimethylamine.

Regarding the hydrophilic monomers, non-limiting mention may further be made of:
amides of unsaturated carboxylic acids, for example acrylamide, methacrylamide, and their N-substituted derivatives, such as $C_1$-$C_4$ N-alkyl(meth)acrylamides, for instance, N-methylacrylamide; $C_1$-$C_4$ N,N-dialkyl (meth)acrylamides, such as N,N-dimethylacrylamide;
hydroxyalkyl (meth)acrylates, such as those comprising alkyl groups ranging from 2 to 4 carbon atoms, for instance hydroxyethyl (meth)acrylates;
(meth)acrylates of polyethylene glycol (5 to 100 EO), and of glycol, optionally substituted on their terminal function by a group chosen from alkyl, phosphate, phosphonate and sulphonate groups, (for example, glycerol acrylate, methoxypolyethylene glycol (meth)acrylate (8 or 12 OE) and hydroxypolyethylene glycol (meth)acrylate);
alkoxyalkyl (meth)acrylates, such as ethoxyethyl (meth) acrylates;
(meth)acrylates of polysaccharide, such as sucrose acrylate;
vinylamides, such as vinylacetamide, which may optionally be cyclic, for instance vinyl lactams, such as N-vinylpyrrolidone and N-vinylcaprolactam;
vinyl ethers, such as vinyl methyl ether.

Additionally, non-limiting mention still further may be made of the following hydrophilic monomers:
methacrylamidopropoxytrimethylammoniumbetaine;
N,N-dimethyl-N-methacryloxyethyl-N-(3-sulphopropyl) ammoniumbetaine,
3-methacryloylethoxycarbonylpyridinium
a compound of the formula:

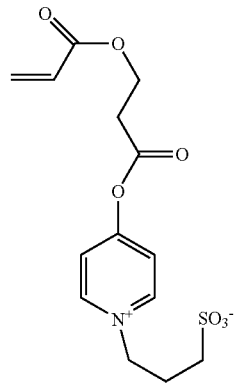

4-vinylpyridiniumsulphopropylbetaine of formula:

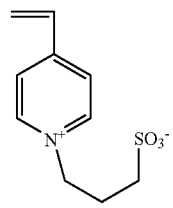

In one aspect of the present disclosure, the hydrophilic monomers are chosen from N,N-dimethylaminoethyl methacrylates (MADAME), acrylic acids, methacrylic acids, crotonic acids, styrenesulphonic acids, acrylamidopropanesulphonic acids, dimethylaminopropylmethacrylamides (DMAPMA), styrene sulphonates, hydroxyethyl acrylates, glycerol acrylates, ethoxyethyl methacrylates, ethoxyethyl acrylates, methoxypolyethylene glycol (meth)acrylates (8 or 12 EO), hydroxypolyethylene glycol (meth)acrylates, N-vinylpyrrolidones, N-vinylcaprolactams, acrylamides, and N,N-dimethylacrylamides.

Among the examples of hydrophobic monomers that can be made hydrophilic, such as by hydrolysis, non-limiting mention may be made of $C_1$-$C_4$ alkyl (meth)acrylates, such as tert-butyl (meth)acrylate and ethyl (meth)acrylate, which can lead to (meth)acrylic acid obtained via hydrolysis.

Among the examples of monomers that create a homopolymer with a Tg less than or equal to 20° C., and, as disclosed herein, some of which can be hydrophilic, non-limiting mention may be made of:
ethylenic hydrocarbons comprising from 2 to 10 carbons, such as ethylene, isoprene, and butadiene;

acrylates with the formula $CH_2=CHCOOR_1$, wherein $R_1$ can be chosen from saturated or unsaturated hydrocarbon groups comprising from 1 to 12 carbons, which may be linear and branched with the exception of the tert-butyl group, and optionally comprising at least one heteroatom chosen from O, N, S and Si, wherein the alkyl group, may optionally be substituted by at least one substituent chosen from hydroxyl groups and halogen atoms (such as Cl, Br, I and F), non-limiting examples of groups $R_1$ may be chosen from are methyl, ethyl, propyl, butyl, isobutyl, hexyl, ethylhexyl, octyl, lauryl, isooctyl, isodecyl, hydroxyethyl, hydroxypropyl, methoxyethyl, ethoxyethyl, methoxypropyl ethylperfluorooctyl, and propylpolydimethylsiloxane groups, $R_1$ can also be chosen from groups of the formula: $—(R'')x-(OC_2H_4)_n—OR'$, wherein x is an integer chosen from 0 and 1, $R''$ is chosen from saturated and unsaturated, linear and branched hydrocarbon groups, comprising from 1 to 12 carbons, n is an integer chosen from 5 to 100, and $R'$ is chosen from H atoms and $CH_3$. For example, $R_1$ can be a methoxy (POE)8-stearyl group;

methacrylates of formula: $CH_2=C(CH_3)—COOR_2$ wherein $R_2$ may be chosen from saturated and unsaturated, linear and branched hydrocarbon groups, comprising from 3 to 12 carbons, and optionally comprising at least one heteroatom chosen from O, N, S and Si, and wherein $R_2$ may optionally be substituted with at least one substituent chosen from hydroxyl groups and halogen atoms (such as, Cl, Br, I, F), non-limiting examples of groups from which $R_2$ may be chosen are hexyl, ethylhexyl, octyl, lauryl, isooctyl, isodecyl, dodecyl, methoxyethyl, methoxypropyl, ethoxyethyl; ethylperfluorooctyl, and propylpolydimethylsiloxane groups, $R_2$ can also be chosen from groups of the formula $—(R'')x-(OC_2H_4)_n—OR'$, wherein x is an integer chosen from 0 and 1, $R''$ is chosen from saturated and unsaturated, linear and branched hydrocarbon groups, comprising from 1 to 12 carbons, n is an integer chosen from 5 to 100, and $R'$ is chosen from H and $CH_3$; (for example, $R_2$ may be a methoxy(POE)8-stearyl group;

the N- or N,N-substituted derivatives of amides of $C_{1-12}$ unsaturated carboxylic acids, such as $C_{1-12}$ N-alkyl (meth)acrylamides, for instance N-octylacrylamide;

vinyl esters of formula: $R_3—CO—O—CH=CH_2$ wherein $R_3$ is chosen from linear and branched alkyl groups comprising from 2 to 12 carbons, and examples of such vinyl esters include vinyl propionate, vinyl butyrate, vinyl ethylhexanoate, vinyl neononanoate, and vinyl neododecanoate;

vinyl alkyl ethers comprising from 1 to 12 carbons, such as vinyl methyl ether, and vinyl ethyl ether.

Additionally, the monomers with Tg less than or equal to 20° C. may be chosen from:

isoprene and butadiene;

methyl, ethyl, isobutyl, n-butyl, ethylhexyl, methoxyethyl, ethoxyethyl and hydroxypolyethylene glycol acrylates;

ethoxyethyl, hexyl, ethylhexyl and hydroxypolyethylene glycol methacrylates;

$C_6-C_{12}$ N-alkyl(meth)acrylamides, such as N-octylacrylamide;

vinyl esters with the formula: $R_3—CO—O—CH=CH_2$ wherein $R_3$ is chosen from linear or branched alkyl groups comprising from 6 to 12 carbons, such as vinyl neononanoate and vinyl neododecanoate.

Among the monomers that can form a homopolymer with a Tg greater than or equal to 20° C., which may be hydrophilic, as disclosed herein, non-limiting mention may be made of:

vinyl compounds of the formula: $CH_2=CH—R_4$, wherein $R_4$ is chosen from hydroxyl group; $—NH—C(O)—CH_3$ group, $—OC(O)—CH_3$ group, $C_3-C_8$ cycloalkyl groups; $C_6-C_{20}$ aryl groups; $C_7-C_{30}$ aralkyl groups ($C_1-C_4$ alkyl groups); heterocyclic groups comprising from 4 to 12 chain members comprising at least one heteroatom chosen from O, N and S; heterocyclylalkyl groups ($C_1-C_4$ alkyl), such as furfuryl group; and wherein the cycloalkyl, aryl, aralkyl, heterocyclic, and heterocyclylalkyl groups may optionally be substituted by at least one substituent chosen from hydroxyl group, halogen atoms, and linear and branched alkyl groups comprising from 1 to 4 carbon atoms, and optionally comprising at least one heteroatom chosen from O, N, S and P, and wherein the alkyl groups may also optionally be substituted by at least one substituent chosen from hydroxyl groups, halogen atoms (such as Cl, Br, I and F) and Si, non-limiting examples of vinyl monomers that may be used include: vinylcyclohexane, styrene and vinyl acetate;

acrylates of the formula $CH_2=CH—COOR_5$, wherein $R_5$ may be chosen from a tert-butyl group, $C_3-C_8$ cycloalkyl groups; $C_6-C_{20}$ aryl groups; $C_7-C_{30}$ aralkyl groups ($C_1-C_4$ alkyl groups); heterocyclic groups comprising from 4 to 12 chain members comprising at least one heteroatom chosen from O, N, and S; heterocyclylalkyl groups ($C_1-C_4$ alkyl), such as furfuryl groups; wherein the cycloalkyl, aryl, aralkyl, heterocyclic and heterocyclylalkyl groups may optionally be substituted by at least one substituent chosen from hydroxyl groups, halogen atoms, and $C_1-C_4$ linear or branched alkyl groups, wherein the alkyl groups may optionally comprise at least one heteroatom chosen from O, N, S and P, and wherein the alkyl groups, may optionally be substituted by at least one substituent chosen from hydroxyl groups, halogen atoms (such as Cl, Br, I and F), and Si, non-limiting examples of the acrylate monomers include: t-butylcyclohexyl, tert-butyl, t-butylbenzyl, furfuryl and isobornyl acrylates;

methacrylates of the formula $CH_2=C(CH_3)—COOR_6$, wherein $R_6$ is chosen from linear and branched alkyl groups comprising from 1 to 4 carbon atoms, such as methyl, ethyl, propyl and isobutyl groups, wherein the alkyl groups may optionally be substituted by at least one substituent chosen from hydroxyl groups, halogen atoms (such as Cl, Br, I and F), Si; $C_3-C_8$ cycloalkyl groups; $C_6-C_{20}$ aryl groups; $C_7-C_{30}$ aralkyl groups ($C_1-C_4$ alkyl group); heterocyclic groups comprising from 4 to 12 chain members comprising at least one heteroatom chosen from O, N, and S; heterocyclylalkyl groups ($C_1-C_4$ alkyl), such as furfuryl groups; wherein the cycloalkyl, aryl, aralkyl, heterocyclic, and heterocyclylalkyl groups may optionally be substituted by at least one substituent chosen from hydroxyl groups, halogen atoms, and linear and branched alkyl groups comprising from 1 to 4 carbon atoms, and optionally comprising at least one heteroatom chosen from O, N, S and P, and wherein the alkyl groups may be optionally substituted by at least one substituent chosen from hydroxyl groups and halogen atoms (such as, Cl, Br, I and F), non-limiting examples of methacrylate monomers include:

methyl, ethyl, n-butyl, isobutyl, t-butylcyclohexyl, t-butylbenzyl, methoxyethyl, methoxypropyl and isobornyl methacrylates;

(meth)acrylamides of the formula: $CH_2=C(R')—CO—NR_7R_8$, wherein $R_7$ and $R_8$, which may be identical or different, may be chosen from hydrogen and linear and branched alkyl groups comprising from 1 to 12 carbon atoms, such as n-butyl, t-butyl, isopropyl, isohexyl, isooctyl, and isononyl groups, and R' may be chosen from hydrogen and methyl. Non-limiting examples of (meth)acrylamide monomers include: N-butylacrylamide, N-t-butylacrylamide, N-isopropylacrylamide, N,N-dimethylacrylamide and N,N-dibutylacrylamide.

Additionally, non-limiting examples of monomers with Tg greater than or equal to 20° C. can be chosen from:

furfuryl, isobornyl, tert-butyl, tert-butylcyclohexyl and tert-butylbenzyl acrylates;

methyl, n-butyl, ethyl and isobutyl methacrylates, styrene, styrene sulphonate;

vinyl acetate and vinylcyclohexane.

A person of ordinary skill in the art should be able to select the monomers and their amounts in relation to the desired result, on the basis of his or her general knowledge, and, for instance, the relative reactivity of each monomer.

Thus, if the desired copolymer is one that has hydrophilic units at the centre of a polymer chain, preference should be given to a bifunctional initiator and a mixture of monomers such that the reactivity of the hydrophilic monomers is greater than that of the other monomers.

Furthermore, the methods of preparation employed can make it possible to adjust and control the Tg value or values of the copolymer, and thus obtain a gradient copolymer having at least one Tg value as disclosed herein.

The gradient copolymers, as disclosed herein, can be prepared by a person of ordinary skill in the art by employing the following procedure:

1) Prepare a mixture of the various monomers, in a solvent if necessary, such as in a stirred reactor. Add a radical polymerization initiator and a polymerization-control agent. One may want to keep the mixture under an atmosphere of gas that is inert with respect to radical polymerization, such as nitrogen or argon. If a polymerization solvent is required, one may choose from alkyl acetates, such as butyl acetate and ethyl acetate, aromatic solvents, such as toluene, ketone solvents, such as methyl ethyl ketone, and alcohols, such as ethanol. In the case when the mixture of monomers is miscible with water, the latter can be used, for example, as solvent or co-solvent.

2) While stirring, bring the mixture up to the desired polymerization temperature. The temperature most frequently, can range from 10° C. to 160° C., such as from 25° C. to 130° C. The choice of polymerization temperature is optimized, for instance, in relation to the chemical composition of the monomer mixture. Thus, monomers that have very high constants of propagation kinetics and a lower affinity for the control agent may be polymerized, for example, at low temperature (for example in the case of a high proportion of methacrylic derivatives, polymerization will probably occur at a temperature ranging from 25° C. to 80° C.).

3) If necessary, one can modify the polymerization medium during polymerization, before reaching 90% conversion of the initial monomers, by supplementary addition of at least one monomer, especially of the initial mixture. Such an addition can be done in various ways, ranging from a single abrupt addition to continuous addition throughout the polymerization.

4) Stop the polymerization once the desired degree of conversion is reached. The overall composition of the copolymer depends on the degree of conversion. One may wish to stop polymerization, for example, after reaching at least 50% conversion, or, such as after reaching at least 60% conversion, or after reaching, for example, at least 90% conversion.

5) Any residual monomers can be removed by any known method, such as by evaporation, or by adding an amount of conventional polymerization initiator, such as peroxide or azo derivatives.

As disclosed herein, the polymerization-control agent that can be used may be chosen from nitroxides of formula (I), either alone or in a mixture:

wherein:

R and R', which may be identical or different, are chosen from linear and branched saturated hydrocarbon (alkyl) groups, comprising from 1 to 40 carbon atoms, which may be optionally substituted by at least one group chosen from $—OR_3$, $—COOR_3$ and $—NHR_3$ (wherein $R_3$ is chosen from H and linear and branched, saturated hydrocarbon (alkyl) groups, comprising 1 to 40 carbon atoms), and wherein R and R' may additionally be joined so as to form a ring.

For example, R and R', which may be identical or different, can be chosen from linear and branched alkyl groups comprising from 1 to 12 carbon atoms, such as methyl, ethyl, propyl, n-butyl, isobutyl, tert-butyl and pentyl groups. For example, R and R' may both be tert-butyl groups;

R" is chosen from a monovalent group of molecular weight (Mw) greater than 16 g/mol, such as a phosphorus-comprising group of the formula:

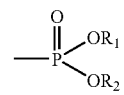

wherein $R_1$ and $R_2$, which may be identical or different, are chosen from linear and branched, saturated hydrocarbon (alkyl) groups, comprising from 1 to 40 carbon atoms, and optionally substituted by at least one group chosen from $—OR_3$, $—COOR_3$ and $—NHR_3$ (wherein $R_3$ is chosen from hydrogen and linear and branched, saturated hydrocarbon (alkyl) groups, comprising from 1 to 40 carbon atoms), and wherein $R_1$ and $R_2$ can additionally be joined so as to form a ring.

For example, $R_1$ and $R_2$, which may be identical or different, may be chosen from linear and branched alkyl groups comprising from 1 to 12 carbon atoms, such as methyl, ethyl, propyl, n-butyl, isobutyl, tert-butyl and pentyl groups. For example, $R_1$ and $R_2$ can both be ethyl groups.

The radical polymerization initiator can be chosen from all the usual polymerization initiators, such as compounds of the azo type, such as azobisisobutyronitrile, and of the peroxide type, such as organic peroxides comprising 6 to 30 carbon atoms, for instance, benzoyl peroxide.

For example, a nitroxide to initiator molar ratio ranging from 1:1 to 2.5:1 can be observed; this ratio can also range from 2 to 2.5 when it is considered that one mole of initiator gives rise to two moles of polymer chains, and can range from 1 to 1.25 for monofunctional initiators.

Certain alkoxyamines can also be used as a radical polymerization initiator, and can be used, for instance, for initiating polymerization and at the same time releasing the nitroxide controlling the polymerization. As disclosed herein, alkoxyamines can be chosen from those of formula (II):

wherein:
R, R' and R" are as defined above for the nitroxide of formula (I),
n is an integer less than or equal to 8, such as, ranging from 1 to 3;
Z is a monovalent or polyvalent radical, such as styryl, acryl and methacryl radicals.

It is also possible to add a nitroxide of formula (I) to the alkoxyamine of formula (II), in an amount ranging from 0 to 20 mol % relative to the moles of alkoxyamine functions (one mole of polyvalent alkoxyamine supplies a number of alkoxyamine functions proportional to its valency), so as to improve the quality of polymerization control.

A person of ordinary skill in the art should be able to select the initiator in relation to the requirements of the present disclosure. Thus, a monofunctional initiator will lead to asymmetric chains, whereas a polyfunctional initiator will lead to macromolecules having a symmetry about a center.

The at least one film-forming gradient copolymer, as disclosed herein, can be present in the haircare compositions in an amount ranging from 0.1% to 60% by weight, relative to the total weight of the composition, such as in an amount ranging from 0.5% to 40% by weight, relative to the total weight of the composition, for instance, in an amount ranging from 1% to 35% by weight, relative to the total weight of the composition, or such as in an amount ranging from 5% to 30% by weight, relative to the total weight of the composition.

The at least one film-forming gradient copolymer can be present in the composition in dissolved form, for example in water or an organic solvent, or alternatively in the form of an aqueous or organic dispersion. It is possible to prepare an aqueous solution of the at least one film-forming gradient copolymer directly by mixing the polymer with water and heating it if necessary.

It is also possible to dissolve the film-forming gradient copolymers in an organic solvent with a boiling point below that of water (for example acetone or methyl ethyl ketone) and at a solids content ranging from 20% to 90% by weight, relative to the total weight of the composition.

When the hydrophilic monomers are chosen from acids, then, if desired, a solution of at least 1M of base, such as salts of hydroxonium ions (OH$^-$), amines (ammonia), carbonates (CO$_3^{2-}$) and hydrogen carbonates (HCO$_3^-$) or of organic neutralizing agents, can be added to the organic solution. When the hydrophilic monomers are chosen from amines, it is possible to add a solution, for instance, at least 1M, of acid. While stirring vigorously, water can then be added to the solution, wherein the solids content obtained ranges from 1 and 80% by weight, relative to the total weight of the composition. If necessary, the water can be replaced with a water/alcohol mixture, in proportions ranging from 99/1 to 50/50. The solvent is evaporated while stirring the solution at 100° C. Thus, concentration is continued until the desired solids content is obtained.

In general, a polymer is considered to be soluble when it forms a clear solution, at 1% by weight, relative to the total weight of the composition and at 25° C. Also, in general, a polymer is considered to be dispersible when it forms a stable suspension of fine, generally spherical particles with an average size, such as less than 1 micron, such as ranging from 5 to 400 nm, further, ranging from 10 to 250 nm, at 1% by weight, relative to the total weight of the composition and at 25° C., measured by light scattering.

According to one aspect of the disclosure, the composition, as disclosed herein, is able to form a film that meets at least one of the following conditions:
a strain at break $\epsilon_r$ ranging from 5% to 2500%, for example from 10% to 2000% and further for example, from 15% to 1000%,
a Young's modulus ranging from 0.5 to 1200 MPa, for example, from 1 to 1000 MPa, and further for example, from 2 to 800 MPa, and
an instantaneous elastic recovery $\epsilon_i$ greater than or equal to 10%, such as greater than or equal to 25%, for instance, greater than or equal to 35%, and ranging from 10% to 100%, for example from 25% to 98%, or further, for example, from 35% to 95%.

The mechanical properties of the film can be measured in monotonic tension in accordance with ASTM Standards, volume 06.01 D 2370-92 'Standard Test Method for Tensile Properties of Organic Coatings'.

To measure the properties, a test piece can be cut from the free film obtained by drying a solution of the copolymer in a suitable solvent, for example water, the amount of the solution being adjusted to obtain, in a Teflon die, a film having a thickness of 150±50 μm at 23±2° C., at a relative humidity of 55%±5%, and at a drying time of 48 hours.

The test piece can be in a dumbbell shape, with useful length 33 mm and useful width 6 mm. The cross-sectional area (s) of the test piece is defined as: s=width×thickness (mm$^2$).

The tests are performed on a tensile tester equipped with an optical extensometer for measurement of the displacement, which is sold under the name Zwick Z010. The measurements are taken at a temperature of 23±2° C. and a relative humidity of 55±5%. The test pieces are stretched at a pulling speed of 50 mm/min. Therefore the pulling speed is set, and the length (L) of the test piece and the force (f) required to produce this length are measured simultaneously.

The length (L) is measured with an optical extensometer using adhesive dots placed on the dumbbell test piece. The initial distance between these two dots defines the useful length Lo used for calculating the strain:

$\epsilon = (L/Lo) \times 100$ expressed in %

A curve of stress (=f/s) as a function of the strain $\epsilon$ is thus obtained, the test being continued until the test piece breaks. The strain at break $\epsilon_r$ corresponds to the maximum strain of the test piece before the point of rupture.

Young's modulus (modulus of elasticity), expressed in MPa, corresponds to the slope of the curve $\sigma = f(\epsilon)$, considered in the linear part of the curve (i.e., the start of the test).

The elastic recovery (R, given in %) is determined by stretching the test pieces at a pulling speed of 50 mm/min until the strain is 100%, i.e., until they are twice their initial length. Then the stress is released, setting a speed of return equal to the pulling speed, i.e., 50 mm/min. The instantaneous elastic recovery ($R_i=\epsilon_i$) is determined by measuring the elongation of the test piece (expressed in % relative to the initial length) immediately after return to zero load. It is therefore defined by the residual instantaneous strain, at zero stress: $\epsilon_{iR}$. Thus the instantaneous elastic recovery ($R_i=\epsilon_i$) is defined by $R_i=\epsilon_i=100-\epsilon_{iR}$.

The cosmetic compositions, as disclosed herein, comprise, in addition to the at least one film-forming gradient copolymer, a cosmetically acceptable medium, i.e., a medium that is compatible with keratinous substances, such as the hair. This medium can be chosen from water; cosmetically acceptable organic solvents, for example $C_1$-$C_4$ alcohols, for instance, ethanol, isopropanol, tert-butanol and n-butanol, and alkylene glycols, such as propylene glycol; and mixtures of water and at least one cosmetically acceptable organic solvent.

The composition of the cosmetically acceptable medium and its proportion in the final haircare composition can be such that the total content of volatile organic compounds (VOC) in the haircare composition is, for example, less than or equal to 55% by weight, relative to the total weight, such as less than or equal to 35% by weight, relative to the total weight, or, further for example, equal to 0%.

Water, or the mixture of water and hydrophilic organic solvents, can therefore be present in the composition, as disclosed herein, in an amount ranging from 0.1% to 99% by weight, relative to the total weight of the composition, for example, in an amount ranging from 10% to 80% by weight, relative to the total weight of the composition.

The haircare compositions, as disclosed herein, additionally can comprise at least one cosmetic or formulation ingredient, generally used in the cosmetics field.

As examples of, additional cosmetic or formulations ingredients, non-limiting mention may be made of: anionic, cationic, nonionic and amphoteric film-forming polymers; fixing polymers; volatile and non-volatile silicones; anionic, cationic, amphoteric and nonionic surfactants; thickeners; pearlescent agents; UV filters; free-radical scavengers; perfumes; preservatives; pigments and colorants; pH adjusters; solubilizers; plasticizers; anti-foaming agents; waxes and oils; vitamins; conditioning agents; organic and mineral particles; synthetic particles and particles of natural origin.

A person of ordinary skill in the art will be able to choose any supplementary additive or additives and/or their quantities in such a way that the intrinsic advantageous properties of the compositions as disclosed herein, are not adversely affected by the addition or additions envisaged.

The film-forming, fixing polymers that can be used in the composition as disclosed herein, can be of natural origin, and possibly modified, or of synthetic origin. The fixing polymers can be chosen from cationic, anionic, nonionic and amphoteric fixing polymers.

Among the cationic fixing polymers, non-limiting mention may be made of polymers comprising primary, secondary, tertiary and/or quaternary amine groups forming part of the polymer chain, or directly linked to the polymer chain, and having a number-average molecular weight ranging from 500 to about 5,000,000, for instance, ranging from 1,000 to 3,000 000, such as:

(1) the homopolymers and copolymers derived from acrylic and methacrylic esters and amides, and comprising units corresponding to at least one of the following formulae:

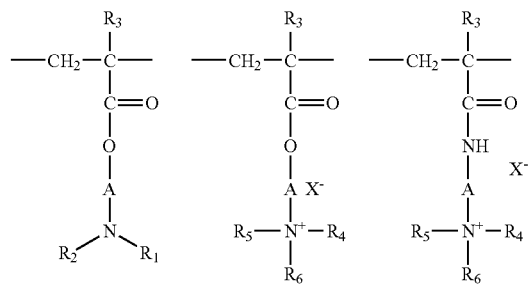

wherein:
$R_1$ and $R_2$, which may be identical or different, can be chosen from hydrogen and $C_1$-$C_6$ alkyl groups;
$R_3$ is chosen from hydrogen and a $CH_3$ group;
A is chosen from linear and branched alkyl groups comprising from 1 to 6 carbon atoms, and a hydroxyalkyl group comprising from 1 to 4 carbon atoms;
$R_4$, $R_5$ and $R_6$, which may be identical or different are chosen from alkyl groups comprising from 1 to 18 carbon atoms and benzyl groups;
X is chosen from methosulphate anions and halides, such as chloride and bromide,
The copolymers of family (1) additionally comprise at least one unit derived from comonomers chosen from the family of acrylamides, methacrylamides, diacetoneacrylamides, acrylamides and methacrylamides substituted on the nitrogen by lower alkyl groups, (meth) acrylic acids or their esters, vinyl lactams, such as vinylpyrrolidone or vinylcaprolactam, vinyl esters.

Thus, among the copolymers of family (1) non-limiting mention may be made of:
copolymers of acrylamide and of dimethylaminoethyl methacrylate quaternized with dimethyl sulphate or with a methyl halide, such as that sold under the name HERCOFLOC® by the company HERCULES,
copolymers of acrylamide and of methacryloyloxyethyltrimethylammonium chloride described, for example, in Patent Application No. EP A-080976 and sold under the name BINA QUAT® P100 by the company CIBA GEIGY,
the copolymer of acrylamide and of methacryloyloxyethyltrimethylammonium methosulphate sold under the name RETEN® by the company HERCULES,
the vinylpyrrolidone/dialkylaminoalkyl acrylate or methacrylate copolymers, which may or may not be quaternized, such as the products sold under the name GAFQUAT® by the company ISP, for example GAFQUAT® 734 and GAFQUAT® 755, or the products called "COPOLYMER® 845, 958 and 937". These polymers are described in detail in French Patents Nos. FR 2 077 143 and FR 2 393 573,
the dimethylaminoethyl methacrylate/vinylcaprolactam/vinylpyrrolidone terpolymers, such as the product marketed under the name GAFFIX® VC 713 by the company ISP, and
the vinylpyrrolidone/quaternized dimethylaminopropyl methacrylamide copolymers, such as the product marketed under the name GAFQUAT® HS 100 by the company ISP.

(2) The quaternized polysaccharides described, for example, in U.S. Pat. Nos. 3,589,578 and 4,031,307, such as guar gums comprising cationic trialkylammonium groups. Such products are marketed for example, under the names JAGUAR C13S, JAGUAR C15 and JAGUAR C17 by the company MEYHALL.

(3) Quaternary copolymers of vinylpyrrolidone and of vinylimidazole, such as the products sold by the company BASF under the name LUVIQUAT TFC.

(4) Chitosans and their salts, such as chitosan acetate, lactate, glutamate, gluconate and pyrrolidone-carboxylate.

Among these compounds, non-limiting mention may be made of chitosan comprising a degree of deacetylation of 90.5% by weight, relative to the total weight of the composition, sold under the name KYTAN BRUT STANDARD by the company ABER TECHNOLOGIES, and the chitosan pyrrolidone-carboxylate sold under the name KYTAMER® PC by the company AMERCHOL.

(5) Cationic cellulose derivatives, such as copolymers of cellulose, and derivatives of cellulose grafted with a water-soluble monomer comprising a quaternary ammonium, and described, for example, in U.S. Pat. No. 4,131,576, such as hydroxyalkylcelluloses, e.g., hydroxymethylcelluloses, hydroxyethylcelluloses and hydroxypropylcelluloses grafted for instance, with a salt of methacryloyloxyethyltrimethylammonium, of methacrylamidopropyltrimethylammonium or of dimethyldiallylammonium. These polymers are sold, for instance, under the names CELQUAT® L200 and CELQUAT® H100 by the company NATIONAL STARCH.

Among the anionic fixing polymers, non-limiting mention may be made of those that have groups derived from carboxylic acid, sulphonic acid, and phosphoric acid and have a number-average molecular weight ranging from 500 to 5,000,000.

The carboxylic groups of the anionic fixing polymers are chosen from monomeric unsaturated mono- and di-carboxylic acids, such as those conforming to the formula:

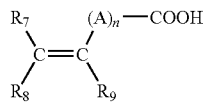

wherein n is an integer ranging from 0 to 10,

A is a methylene group, which may be optionally linked to the carbon atom of the unsaturated group, or to the adjacent methylene group when n is greater than 1, via a heteroatom, such as oxygen or sulphur, $R_7$ is chosen from hydrogen, phenyl groups and benzyl groups, $R_8$ is chosen from hydrogen, lower alkyl groups, and carboxyl groups, and $R_9$ is chosen from hydrogen, lower alkyl groups, —$CH_2$—COOH groups, phenyl groups, and benzyl groups.

In the above carboxylic acid formula, a lower alkyl group, for example, may be chosen from a group comprising from 1 to 4 carbon atoms, such as methyl and ethyl groups.

Among the anionic fixing polymers comprising carboxyl groups as disclosed herein, non-limiting mention may be made of:

A) The homo- and copolymers of acrylic and methacrylic acid, and the salts thereof, such as the products sold under the names VERSICOL® E or K by the company ALLIED COLLOID, and ULTRAHOLD® by the company BASF, the copolymers of acrylic acid and acrylamide sold as sodium salt under the names RETEN® 421, 423 or 425 by the company HERCULES, and the sodium salts of polyhydroxycarboxylic acids.

B) The copolymers of acrylic and methacrylic acid comprising a mono-ethylenic monomer, such as ethylene, styrene, vinyl esters, esters of acrylic and methacrylic acid, optionally grafted on a polyalkyleneglycol, such as polyethylene glycol, and optionally crosslinked. Such polymers are described, for example, in French Patent No. FR 1 222 944 and German Patent Application No. DE 2 330 956, wherein the copolymers of this type have in their chain an acrylamide unit that is optionally N-alkylated and/or N-hydroxyalkylated, such as those described, for example, in Luxembourg Patent Applications Nos. 75370 and 75371 and offered under the name QUADRAMER® by the company AMERICAN CYANAMID. Additionally, non-limiting mention may be made of the copolymers of acrylic acid and of $C_1$-$C_4$ alkyl methacrylate, and the terpolymers of vinylpyrrolidone, acrylic acid and $C_1$-$C_{20}$ alkyl methacrylate, for instance lauryl methacrylate, such as that marketed by the company ISP under the name ACRYLIDONE® LM and the methacrylic acid/ethyl acrylate/tert-butyl acrylate terpolymers, such as the product marketed under the name LUVIMER® 100 P by the company BASF.

C) The copolymers derived from crotonic acid, such as those whose chain comprises vinyl acetate or propionate units, and possibly other monomers, such as allylic and/or methallylic esters, vinyl ethers and vinyl esters of a saturated, linear or branched type, carboxylic acid comprising a long hydrocarbon chain, such as those comprising at least 5 carbon atoms, these polymers possibly being grafted and crosslinked, or alternatively some other vinylic, allylic or methallylic ester monomer of an α- or β-cyclic carboxylic acid. Such polymers are described inter alia in French Patent Nos. FR 1 222 944, FR 1 580 545, FR 2 265 782, FR 2 265 781, FR 1 564 110 and FR 2 439 798. Commercial products included in this class are the resins 28-29-30, 26-13-14 and 28-13-10 marketed by the company NATIONAL STARCH.

D) Copolymers derived from $C_4$-$C_8$ mono-unsaturated carboxylic acids and anhydrides that may be chosen from:

copolymers comprising (i) at least one monomeric residue of maleic, fumaric, and itaconic acids and/or anhydrides and (ii) at least one monomeric residue resulting from monomers chosen from vinyl esters, vinyl ethers, vinyl halides, phenylvinylic derivatives, acrylic acid and its esters, wherein the anhydride functions of these copolymers can optionally be mono-esterified or mono-amidified. Such polymers are described, for example, in U.S. Pat. Nos. 2,047,398, 2,723,248 and 2,102,113, and Patent No. GB 839 805.

Further examples include the commercial products such as those sold under the names GANTREZ® AN or ES by the company ISP.

Copolymers comprising (i) at least one unit chosen from maleic, citraconic, and itaconic anhydride units and (ii) at least one monomer chosen from allylic and methallylic esters optionally comprising at least one groups chosen from acrylamides, methacrylamides, α-olefin groups, acrylic and methacrylic esters, acrylic and methacrylic acids, and vinylpyrrolidones in their chain, and wherein the anhydride functions of the copolymers are optionally mono-esterified or mono-amidified.

These polymers are described, for example, in French Patent Nos. FR 2 350 384 and FR 2 357 241 of the Applicant.

E) Polyacrylamides comprising carboxylate groups.

Polymers comprising sulphonic groups that may be used are polymers comprising at least one unit chosen from vinyl-sulphonic, styrene-sulphonic, naphthalene-sulphonic and acrylamido-alkylsulphonic units.

As non-limiting examples, the polymers can be chosen from:
- the salts of polyvinylsulphonic acid having a molecular weight ranging from 1,000 to 100,000, as well as the copolymers comprising an unsaturated comonomer, such as acrylic and methacrylic acids and their esters, as well as acrylamide and its derivatives, vinyl ethers and vinylpyrrolidone.
- the salts of polystyrene-sulphonic acid, such as the sodium salts sold, for example, under the names FLEXAN® 130 and FLEXAN® 500 by the company NATIONAL STARCH. These compounds are described in French Patent No. FR 2 198 719.
- the salts of polyacrylamide-sulphonic acids such as those mentioned in U.S. Pat. No. 4,128,631, and, for example, the polyacrylamidoethylpropanesulphonic acid sold under the name COSMEDIA POLYMER® HSP 1180 by the company HENKEL.

Among the amphoteric fixing polymers, non-limiting mention may be made of those comprising B and C units randomly distributed in the polymer chain, wherein B comprises at least one unit derived from a monomer comprising at least one basic nitrogen atom, and C comprises at least one unit derived from a monomer comprising at least one group chosen from carboxylic and sulphonic group. The amphoteric fixing polymers can also comprise zwitterionic units chosen from carboxybetaine and sulphobetaine units.

The amphoteric fixing polymers may also be polymers comprising a cationic main chain comprising at least one groups chosen from primary, secondary, tertiary and quaternary amine groups, wherein at least one amine group carries, via a hydrocarbon radical, an acid chosen from carboxylic acid and sulphonic acid groups. The amphoteric fixing polymers can also comprise an anionic chain derived from α,β-unsaturated carboxylic acids, wherein at least one carboxyl group has been made to react with a polyamine comprising at least one primary amine group.

Amphoteric fixing polymers according to the disclosure given above can be chosen, for example, from the following polymers:

(1) the polymers resulting from the copolymerization of a monomer derived from a vinylic compound bearing a carboxyl group, such as acrylic acid, methacrylic acid, maleic acid, alpha-chloroacrylic acid, and of a basic monomer derived from a substituted vinylic compound comprising at least one basic atom, such as dialkylaminoalkyl methacrylate and acrylate, dialkylaminoalkyl methacrylamide and acrylamide. Such compounds are described in U.S. Pat. No. 3,836,537.

(2) polymers comprising units derived from:
(a) at least one monomer chosen from acrylamides and methacrylamides substituted on a nitrogen atom by an alkyl group,
(b) at least one acid comonomer comprising at least one reactive carboxyl group, and
(c) at least one basic comonomer, such as esters, comprising primary, secondary, tertiary and quaternary amine substituents of acrylic and methacrylic acids, and the product of quaternization of dimethylaminoethyl methacrylate with dimethyl or diethyl sulphate.

The N-substituted acrylamides or methacrylamides are, for example, compounds with alkyl groups comprising from 2 to 12 carbon atoms, such as N-ethylacrylamide, N-tert-butylacrylamide, N-tert-octylacrylamide, N-octylacrylamide, N-decylacrylamide, N-dodecylacrylamide, as well as the corresponding methacrylamides.

The acid comonomers can be chosen, for example, from acrylic, methacrylic, crotonic, itaconic, maleic, and fumaric acids as well as the alkyl monoesters comprising from 1 to 4 carbon atoms of maleic or fumaric acids or anhydrides.

In one aspect of the present disclosure, the basic comonomers are chosen from aminoethyl, butylaminoethyl, N,N'-dimethylaminoethyl, and N-tert-butylaminoethyl methacrylates.

In another aspect of the present disclosure, use is made of the copolymers whose CTFA designation (4th edition, 1991) is octylacrylamide/acrylates/butylaminoethyl-methacrylate copolymer, such as the products sold under the name AMPHOMER® or LOVOCRYL® 47 by the company NATIONAL STARCH.

(3) The crosslinked and partially and completely alkoylated polyaminoamides, partially or totally derived from polyaminoamides of general formula:

wherein $R_{10}$ is chosen from divalent groups derived from a saturated dicarboxylic acid, aliphatic monocarboxylic and dicarboxylic acids comprising an ethylenic double bond, esters of lower alkanols comprising from 1 to 6 carbon atoms, of these acids and groups derived from the addition of any one of the acids with a bis-primary or bis-secondary amine, and Z is chosen from a group derived from a bis-primary, mono- or bis-secondary polyalkylene-polyamines and, for example, may be chosen from compounds of the formula:

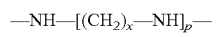

wherein, in the amount ranging from 60 to 100 mol. %, x is equal to 2 and p is an integer chosen from 2 and 3, or alternatively x is equal to 3 and p is equal to 2, and the group is derived from a group chosen from diethylene-triamines, triethylene-tetraamines and dipropylene-triamine;

wherein, in the amount ranging from 0 to 40 mol. %, x is equal to 2 and p is equal to 1 and the group is derived from a group chosen from ethylene-diamines and piperazines:

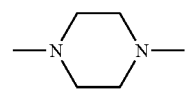

and wherein, in the amount ranging from 0 to 20 mol. %, the group

is derived from hexamethylenediamine,
these polyaminoamides being crosslinked by an addition reaction of a bifunctional crosslinking agent chosen from epihalohydrins, diepoxides, dianhydrides, and bis-unsaturated derivatives, via the use of 0.025 to 0.35 mol of crosslinking agent per amine group of the polyaminoamide, and alkoylated by the action of an acid chosen from acrylic acids, chloroacetic acids alkane-sultones, and the salts thereof.

The saturated carboxylic acids may be chosen, for example, from acids comprising from 6 to 10 carbon atoms, such as adipic, trimethyl-2,2,4-adipic and trimethyl-2,4,4-adipic, terephthalic acids, acids with an ethylenic double bond, for example, acrylic, methacrylic, and itaconic acids.

The alkane-sultones that may be used in alkoylation are, for example, propane- and butane-sultone, and the salts of the alkoylation agentsmay be, for example, salts of sodium or of potassium.

(4) polymers comprising zwitterionic units of formula:

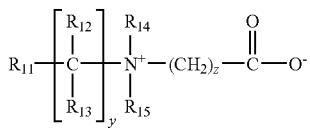

wherein $R_{11}$ is chosen from polymerizable unsaturated groups, such as an acrylate, methacrylate, acrylamide or methacrylamide group, y and z, which may be identical or different, are integers ranging from 1 to 3, $R_{12}$ and $R_{13}$, which may be identical or different, are chosen from hydrogen, and methyl, ethyl, and propyl groups, $R_{14}$ and $R_{15}$, which may be identical or different, are chosen from hydrogen atoms and alkyl groups, provided that the sum of the carbon atoms comprising $R_{14}$ and $R_{15}$ does not exceed 10.

The polymers comprising such units can also comprise units derived from non-zwitterionic monomers, such as dimethyl- and diethylaminoethyl acrylate and methacrylate, and alkyl acrylates and methacrylates, acrylamides and methacrylamides, and vinyl acetate. As a non-limiting example, mention may be made of the methyl methacrylate/methyl dimethylcarboxymethylammonioethylmethacrylate copolymers, such as the product sold under the name DIAFORMER® Z301 by the company SANDOZ.

(5) Polymers derived from chitosan comprising monomer units chosen from the following formulae:

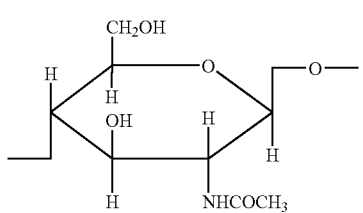

(A)

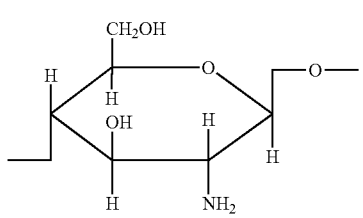

(B)

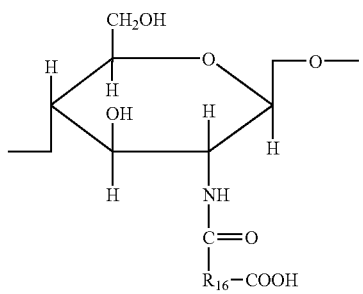

(C)

wherein unit (A) is present in an amount ranging from 0% to 30% by weight, relative to the total weight, unit (B) is present in an amount ranging from 5% to 50% by weight, relative to the total weight, and unit (C) is present in an amount ranging from 30% to 90% by weight, relative to the total weight;

wherein, in the unit (C), $R_{16}$ is chosen from a group of formula:

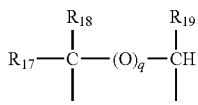

wherein if q is equal to 0, then $R_{17}$, $R_{18}$ and $R_{19}$, which may be identical or different, are chosen from hydrogen, methyl, hydroxyl, acetoxy and amino residues, monoalkoylamine residues and dialkoylamine residues, which may possibly be interrupted by at least one nitrogen atom and/or optionally substituted by at least one group chosen from amine, hydroxyl, carboxyl, alkoylthio, and sulphonic groups, and an alkoylthio residue whose alkoyl group carries an amino residue, wherein if at least one of $R_{17}$, $R_{18}$ and $R_{19}$ is an alkoylthio residue whose alkoyl group carries an amino residue, then at least one other of $R_{17}$, $R_{18}$ and $R_{19}$ must be a hydrogen atom;

if q is equal to 1, then $R_{17}$, $R_{18}$ and $R_{19}$, which may be identical or different, are chosen from hydrogen, as well as the salts formed by these compounds with bases or acids.

(6) The polymers obtained by N-carboxylation of chitosan, such as N-carboxymethylchitosan and N-carboxybutyl-chitosan sold under the name EVALSAN® by the company JAN DEKKER.

(7) The polymers described in French Patent No. 1 400 366 and chosen from those of the formula:

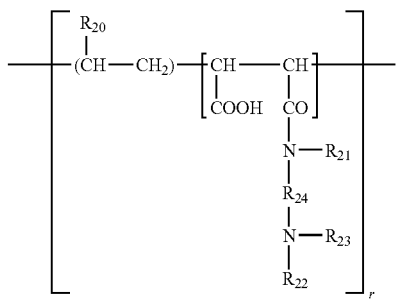

wherein $R_{20}$ is chosen from hydrogen atoms, $CH_3O$, $CH_3CH_2O$ and phenyl groups, $R_{21}$ is chosen from a hydrogen atom and lower alkyl groups, such as methyl and ethyl, $R_{22}$ is chosen from a hydrogen atom and $C_1$-$C_6$ lower alkyl groups, such as methyl and ethyl, $R_{23}$ is chosen from $C_1$-$C_6$ lower alkyl groups, such as methyl, ethyl and groups conforming to the formula: —$R_{24}$—$N(R_{22})_2$, wherein $R_{24}$ is a group chosen from —$CH_2$—$CH_2$—, —$CH_2$—$CH_2$—$CH_2$—, —$CH_2$—$CH(CH_3)$—, and $R_{22}$ is chosen from a hydrogen atom and $C_1$-$C_6$ lower alkyl groups, such as methyl and ethyl.

(8) Amphoteric polymers of the type -D-X-D-X chosen from:
(a) the polymers obtained by the action of chloroacetic acid or sodium chloroacetate on the compounds comprising at least one unit of formula:

-D-X-D-X-D- wherein D is the group

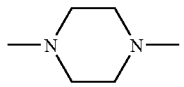

and X is chosen from the symbols E and E', which may be identical or different, and may be chosen from a divalent group which is a straight-chain or branched-chain alkylene group, comprising up to 7 carbon atoms in the main chain, which may be optionally substituted with at least one hydroxyl group and possibly further comprising, at least one group chosen from atoms of oxygen, nitrogen, and sulphur, and 1 to 3 aromatic and heterocyclic rings; wherein the atoms of oxygen, nitrogen and sulphur can be present in the form of a group chosen from ether, thioether, sulphoxide, sulphone, sulphonium, alkylamine, alkenylamine groups, hydroxyl, benzylamine, amine oxide, quaternary ammonium, amide, imide, alcohol, ester and urethane groups.

(b) Polymers of formula:

-D-X-D-X- wherein D is chosen from a group

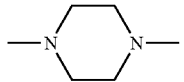

and X is chosen from the symbols E and E', and at least once is chosen from E'; wherein E has the meaning defined above and E' is chosen from straight-chain and branched-chain alkylene divalent groups, comprising up to 7 carbon atoms in the main chain, which may be optionally substituted by at least one hydroxyl group and E' can also comprise at least one nitrogen atom, wherein the nitrogen atom is substituted by an alkyl chain that optionally comprises an oxygen atom, and moreover the straight-chain and branched-chain alkylene divalent groups, comprising up to 7 carbon atoms in the main chain, can comprise at least one functional group chosen from at least one carboxyl and hydroxyl, and wherein the alkyl chain can be betainized by reaction with chloroacetic acid or sodium chloroacetate.

(9) Alkyl($C_1$-$C_5$)vinylether/maleic anhydride copolymers partially modified by semi-amidification with an N,N-dialkylaminoalkylamine, such as N,N-dimethylaminopropylamine or by semi-esterification with an N,N-dialkanolamine. These copolymers can also comprise other vinylic comonomers, such as vinylcaprolactam.

The nonionic fixing polymers can be chosen, for example, from: vinylpyrrolidone,
copolymers of vinylpyrrolidone and vinyl acetate,
polyalkyloxazolines, such as the polyethyloxazolines proposed by the company DOW CHEMICAL under the names PEOX® 50,000, PEOX® 200,000 and PEOX® 500,000,
the homopolymers of vinyl acetate, such as the product proposed under the name APPRETAN® EM by the company HOECHST or the product proposed under the name RHODOPAS® A 012 by the company RHONE POULENC,
copolymers of vinyl acetate and acrylic ester, such as the product proposed under the name RHODOPAS® AD 310 by the company RHONE POULENC,
copolymers of vinyl acetate and ethylene, such as the product proposed under the name APPRETAN® TV by the company HOECHST,
copolymers of vinyl acetate and maleic ester, for example dibutyl maleate, such as the product proposed under the name APPRETAN® MB EXTRA by the company HOECHST,
copolymers of polyethylene and maleic anhydride,
poly(alkyl acrylate)s and poly(alkyl methacrylate)s, such as the product proposed under the name MICROPEARL® RQ 750 by the company MATSUMOTO or the product proposed under the name LUHYDRAN® A 848 S by the company BASF,
copolymers of acrylic esters, such as the copolymers of alkyl acrylates and of alkyl methacrylates, such as the products proposed by the company ROHM & HAAS under the names PRIMAL® AC-261 K and EUDRAGIT® NE 30 D, by the company BASF under the names ACRONAL® 601, LUHYDRAN® LR 8833 or 8845, by the company HOECHST under the names APPRETAN® N9212 and N9213;
copolymers of acrylonitrile and of a nonionic monomer chosen, for example, from butadiene and alkyl (meth) acrylates; we may mention the products proposed under the names NIPOL® LX 531 B by the company NIPPON ZEON or those proposed under the name CJ 0601 B by the company ROHM & HAAS,
polyurethanes, such as the products proposed under the names ACRYSOL® RM 1020 or ACRYSOL® RM 2020 by the company ROHM & HAAS, the products URAFLEX® XP 401 and URAFLEX® XP 402 UZ by the company DSM RESINS,
polyamides, such as the product ESTAPOR® LO 11 proposed by the company RHONE POULENC,
nonionic guar gums, unmodified or chemically modified. Unmodified guar gums are, for example, the products sold under the name VIDOGUM® GH 175 by the company UNIPECTINE and under the name JAGUAR® C. by the company MEYHALL. The modified guar gums are, for example, modified by $C_{1-6}$ hydroxyalkyl groups, such as by hydroxymethyl, hydroxyethyl, hydroxypropyl and hydroxybutyl groups. Such nonionic guar gums possibly modified by hydroxyalkyl groups are, for example, sold under the trade names JAGUAR® HP8, JAGUAR® HP60, JAGUAR® HP120, JAGUAR® DC 293 and JAGUAR® HP 105 by the company MEYHALL, or under the name GALACTOSOL® 4H4FD2 by the company AQUALON.

It is also possible to use, as fixing polymers, film-forming polymers of the grafted silicone type comprising a polysiloxane part and a part consisting of a non-silicone organic chain, with one of the two parts comprising the main chain of the polymer and the other being grafted onto the main chain.

These polymers are, for example, described in Patent Applications Nos. EP A-0 412 704, EP A-0 412 707, EP A-0 640 105 and WO 95/00578, EP A-0582 152 and WO 93/23009 and U.S. Pat. Nos. 4,693,935, 4,728,571 and 4,972,037.

These polymers are, for example, anionic or nonionic.

The polymers are, for example, copolymers that can be obtained by radical polymerization from the mixture of monomers formed by
a) 50% to 90% by weight, of tert-butyl acrylate,
b) 0% to 40% by weight, of acrylic acid,
c) 5% to 40% by weight, of a silicone macromer of formula $$CH_2=\underset{CH_3}{\underset{|}{C}}-\underset{\|}{\overset{O}{C}}-O-(CH_2)_3-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_v\underset{\underset{CH_3}{|}}{\overset{\overset{CH_3}{|}}{Si}}-(CH_2)_3-CH_3$$

wherein v is chosen from a number ranging from 5 to 700, the percentages by weight being calculated relative to the total weight of the monomers.

Other examples of silicone graft polymers, such as polydimethylsiloxanes (PDMS) onto which are grafted, by means of a linkage of the thiopropylene type, mixed polymer units of the poly(meth)acrylic acid type and of the alkyl poly(meth)acrylate type and polydimethylsiloxanes (PDMS) onto which are grafted, by means of a linkage of the thiopropylene type, polymer units of the isobutyl poly(meth)acrylate type.

It is also possible to use polymers comprising urethane units. These polyurethanes can be functionalized or not, and siliconized or not. The polyurethanes under consideration, for example, are those described in Patent Applications Nos. EP 0 751 162, EP 0 637 600, EP 0 648 485 and FR 2 743 297 of which the applicant is the patentee, as well as the Patent Applications Nos. EP 0 656 021 and WO 94/03510 of the company BASF, and in the Patent Application No. EP 0 619 111 of the company National Starch. As polyurethanes that are particularly suitable for the present disclosure, we may mention the products marketed under the names LUVISET-PUR® and LUVISET® Si PUR by the company BASF.

The film-forming fixing polymer or polymers used in the compositions of the present disclosure are present in an amount ranging, for example, from 0.05% to 10% by weight, relative to the total weight of the composition.

When the composition is packaged in a aerosol device, it additionally comprises a propellant, chosen from any liquefiable gas used in aerosol devices, such as dimethyl ether, $C_{3-5}$ alkanes, 1,1-difluoroethane, mixtures of dimethyl ether and $C_{3-5}$ alkanes, and mixtures of 1,1-difluoroethane and dimethyl ether and/or $C_{3-5}$ alkanes.

Dimethyl ether and $C_{3-5}$ alkanes, and, for example, propane, n-butane and isobutane, are preferred for use as propellant.

The propellant is present in an amount ranging, for example, from 35% to 70% by weight, relative to the total weight of the mixture (propellant+hairdressing composition) comprising the aerosol device.

A person skilled in the art will be able to choose the appropriate galenic form, as well as its method of preparation, on the basis of his general knowledge, taking into account on the one hand the nature of the constituents used, such as their solubility in the carrier, and on the other hand the application envisaged for the composition.

The composition, disclosed herein, can be a haircare product, such as for hairdressing and for maintaining a hairstyle. The haircare compositions are, for example, shampoos, gels, setting lotions, blow-drying lotions, fixing and hairdressing compositions, such as lacquers or sprays. The lotions can be packaged in various forms, such as in atomizers, spray bottles or in aerosol containers to provide application of the composition as a spray or as a mousse. Such forms of packaging are indicated, for example, when we wish to obtain a spray or mousse for fixing or treating the hair.

The haircare compositions are, for example, hair lacquers or mousses.

The disclosure is illustrated in more detail in the following examples.

In these examples, the polymerization control agent used was the stable nitroxide, called SG1, with the formula:

$$\underset{EtO}{\overset{EtO}{\underset{\diagdown}{}}}\overset{O}{\underset{\|}{P}}-CH-\underset{CH_3-C-CH_3}{\overset{CH_3}{\underset{|}{\overset{|}{N}}}}-N-O°$$

The polymerization initiators mentioned in the examples were alkoxyamines called "DIAMS" and "MONAMS" which correspond to the following formula:

DIAMS

MONAMS

EXAMPLE 1

Bulk Synthesis of Gradient Copolymer

The mixture of reactants was as follows:
MONAMS: 3.0 g
SG1: 0.18 g
Ethyl acrylate: 480 g (i.e. 80% by weight, relative to the total weight of monomers)
Styrene: 60 g (i.e. 10% by weight, relative to the total weight of monomers)

Methacrylic acid: 60 g (i.e. 10% by weight, relative to the total weight of monomers)

All the constituents were mixed together, without solvent, under a nitrogen atmosphere, then heated to a temperature that was maintained ranging from 110 to 115° C. for 198 minutes. The reaction was stopped at a degree of conversion of 60%.

Figure 3:
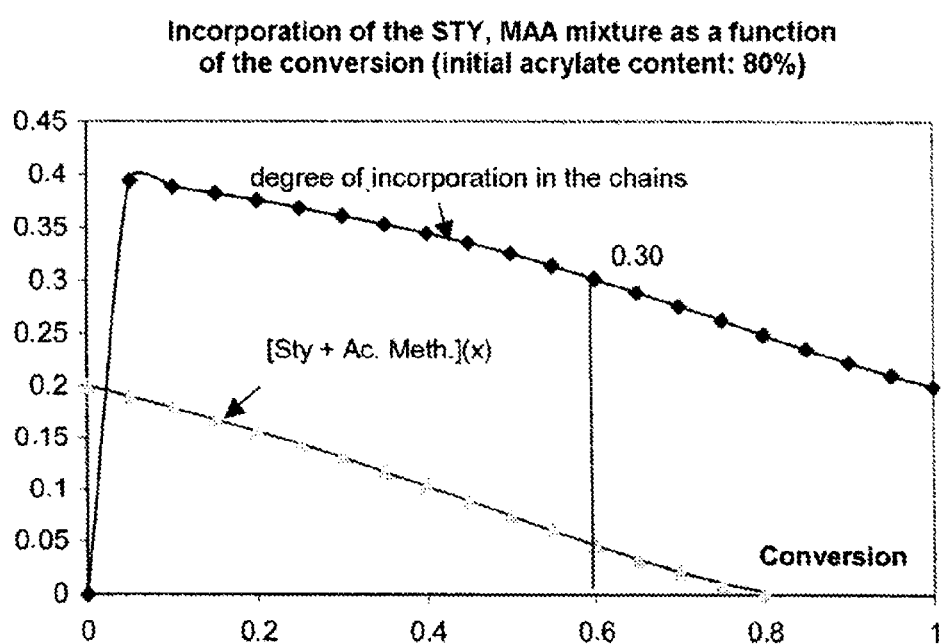
FIG. 3 shows the calculated degree of incorporation of styrene/methacrylic acid mixture in a gradient copolymer as a function of monomer conversion.

Calculation of the gradient by simulation gave the curve shown in FIG. 3. Theoretical prediction gave 30% incorporation of the mixture (styrene/methacrylic acid) and 70% ethyl acrylate.

The validity of this model was provided by monitoring the relative concentrations of the three monomers by gas chromatography and NMR analysis of the polymers.

Using these methods, it was found that at 60% conversion, the final chemical composition of the copolymer was as follows (wt %): 68.4% ethyl acrylate, 16.1% styrene and 15.5% methacrylic acid according to NMR on the calculated curve (69%).

Using LAC, the trace of the polymer showed the low polydispersity of the chemical composition of the chains.

Measurement of the molecular weights by steric exclusion chromatography lead to the following results:

Mn was equal to 32,140 g/mol and Mw was equal to 51,700 g/mol, hence the polydispersity index Ip was equal to 1.6.

The composition dispersity (or w) was 1.6.

Figure 4:
FIG. 4 shows a possible representation of the morphology of a copolymer according to Example 1, wherein the darkened units denote the styrene/methacrylic acid linkages, and the white units denote the ethyl acrylate linkages.

FIG. 4 was a possible schematic representation of the copolymer obtained: wherein the darkened units denote the styrene/methacrylic acid linkages, and the white units denote the ethyl acrylate linkages.

EXAMPLE 2

Bulk Synthesis of Gradient Copolymer

Following the procedure described in Example 1, various copolymers were prepared from the following mixture of reactants:
MONAMS: 3.0 g
SG1: 0.18 g
Styrene: 60 g
Methacrylic acid: 60 g
Acrylate (or acrylate mixture): 480 g

| Example | Acrylate | Characteristics of the copolymer | Final composition of the copolymer (wt %) |
|---|---|---|---|
| 2a | Butyl acrylate | Mn = 31,100 g/mol<br>Mw = 52,930 g/mol<br>Ip = 1.7 | Styrene: 18<br>Methacrylic acid: 22<br>Butyl acrylate: 60 |
| 2b | Methyl acrylate | Mn = 32,750 g/mol<br>Mw = 61,470 g/mol<br>Ip = 1.88 | Styrene: 20<br>Methacrylic acid: 21<br>Methyl acrylate: 59 |
| 2c | Mixture 50/50 by weight butyl acrylate/ethyl acrylate | Mn = 29,690 g/mol<br>Mw = 51,630 g/mol<br>Ip = 1.74 | Styrene: 18<br>Methacrylic acid: 16<br>Acrylates: 66 |

EXAMPLE 3

Synthesis in the Presence of Solvent

The same synthesis as in Example 1 was carried out, but with solvent present. The mixture of reactants was as follows:

MONAMS: 3.43 g
SG1: 0.2 g
Ethyl acrylate: 336 g
Styrene: 42 g
Methacrylic acid: 42 g
Toluene: 180 g All of the constituents were mixed together, in the toluene solvent, under a nitrogen atmosphere, then heated to a temperature that was maintained ranging from 110 to 115° C., for 198 minutes.

The final degree of conversion was 82%, and the solids content obtained was 57.2% by weight.

The following analytical results were found:
Mn was equal to 30,570 g/mol, Mw was equal to 50,500 g/mol and Ip was equal to 1.65. The composition dispersity (or w) was 2.0.

The final composition of the copolymer was found by LAC, which showed similarity of composition with the copolymer prepared in Example 1 and absence of homopolymer in the materials.

EXAMPLE 4

Synthesis in the Presence of Solvent

Following the procedure in Example 3, at 120° C. and for 400 minutes, a new copolymer was synthesized, but in a different solvent: methyl ethyl ketone.

The initial composition of the mixture was:
MONAMS: 4.893 g
SG1: 0.2881 g
Ethyl acrylate: 293.8 g
Methyl acrylate: 32.66 g
Styrene: 76.8 g
Methacrylic acid: 76.8 g
Methyl ethyl ketone: 120 g The final degree of conversion was 99%, and the solids content obtained was 79.9%.

The following analytical results were determined:
Mn was equal to 30,500 g/mol
Mw was equal to 58,000 g/mol
Ip was equal to 1.9

The incorporation of the monomers over time was measured by monitoring the proportions of residual monomers (by %) over the course of time (in minutes) by gas chromatography:

| Time | | 0 | 75 | 130 | 190 | 290 | 400 |
|---|---|---|---|---|---|---|---|
| Overall conversion | | 0 | 16 | 30.5 | 49.5 | 85.4 | 99 |
| residual (%) | MeA | 5.45 | 5.1 | 3.75 | 3.75 | 1.6 | 0.13 |
| | EA | 48.95 | | | | 17.95 | 1.2 |
| | MAA | 12.8 | 12.15 | 4.6 | 2 | 0.35 | 0.08 |
| | S | 12.8 | 12.46 | 6.7 | 3.92 | 0.15 | 0.007 |

EA: ethyl acrylate
MeA: methyl acrylate
S: styrene
MAA: methacrylic acid

The total residual content was calculated, taking into account the solvent, quantified by the solids content.

Figure 5:
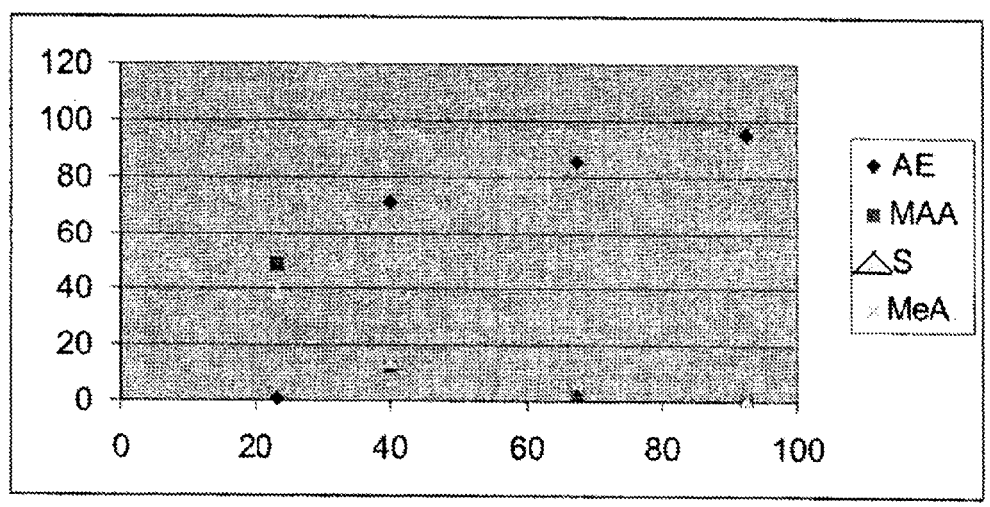
FIG. 5 shows the calculated gradient for each monomer in the gradient copolymer of Example 4.

It was noted that each monomer was present throughout the reaction. The gradient determined for each monomer could then be calculated, and gave the curves as shown in FIG. 5.

The final composition of the copolymer was as follows:
ethyl acrylate: 34% by weight
methyl acrylate: 34% by weight styrene: 16% by weight
methacrylic acid: 16% by weight

EXAMPLE 5

Prepared an aqueous dispersion at 10% solids content of the copolymer prepared in Example 2a.

To do this, the polymer was first dried in the stove. Then, 10 g of polymer, which comprised 1.6 g of AMP (amino-2-methyl-2-propanol), was dissolved in 90 ml of water. A clear, very thin aqueous dispersion was obtained. The particle size, measured by light scattering (Coulter 4NW apparatus), was 33 nm.

EXAMPLE 6

Prepared an aqueous dispersion of the copolymer prepared in Example 1.

Dissolved 10 g of polymer in 40 g of tetrahydrofuran; added 1.41 g of AMP (amino-2-methyl-2-propanol) dissolved in 10 ml of water. The solution became thicker. Then slowly added, while stirring vigorously, 90 ml of demineralized water. The solution remained clear, and became fluid again.

The solvent was evaporated and a clear, thin aqueous dispersion was obtained. The particle size, measured by light scattering (Coulter 4NW apparatus), was 199 nm.

EXAMPLE 7

Prepared aqueous dispersions at 4.6% by weight, of dry matter from the dispersions in Examples 5 and 6.

Then prepared an aerosol spray comprising:
65 g of aqueous dispersion of polymer at 4.6% by weight, of dry matter
35 g of DME (dimethylether)

The lacquer displayed good sprayability, as well as good lacquering power.

EXAMPLE 8

The Young's modulus, strain at break, and instantaneous elastic recovery were determined for the copolymers of Examples 5 and 6.

After drying, a film was obtained that had the following characteristics, measured in accordance with the protocols described above:

|  | Young's modulus | Elongation at break $\epsilon_r$ | Instantaneous elastic recovery $\epsilon_i$ |
| --- | --- | --- | --- |
| Example 5 | 0.5 ± 0.1 MPa | 1000 ± 200% | 40 ± 1% |
| Example 6 | 2 ± 0.1 MPa | 480 ± 50% | 39 ± 2% |

What is claimed is:

1. A hair-cosmetic composition comprising, in a cosmetically acceptable medium, film-forming gradient copolymer containing from 5 to 25 percent by weight of a methacrylic acid monomeric residue, from 50 to 90 percent by weight of an ethyl acrylate monomeric residue, and 5 to 25 percent by weight of a styrene monomeric residue, wherein the film-forming gradient copolymer exhibits a mass polydispersity index (Ip) less than or equal to 2.5,
  and wherein the composition is able to form a film that has at least one of the following characteristics:
    a strain at break $\epsilon_r$ ranging from 5% to 2500%, and/or
    a Young's modulus ranging from 0.5 to 1200 MPa, and/or
    an instantaneous elastic recovery $\epsilon_i$ greater than or equal to 10%.

2. The composition according to claim 1, wherein the film-forming gradient copolymer exhibits a mass polydispersity index (Ip) ranging from 1.1 to 2.3.

3. The composition according to claim 2, wherein the film-forming gradient copolymer exhibits a mass polydispersity index (Ip) ranging from 1.15 to 2.0.

4. The composition according to claim 3, wherein the film-forming gradient copolymer exhibits a mass polydispersity index (Ip) ranging from 1.2 to 1.9.

5. The composition according to claim 1, wherein the composition forms a film that has a strain at break $\epsilon_r$ ranging from 10% to 2000%.

6. The composition according to claim 5, wherein the composition forms a film that has a strain at break $\epsilon_r$ ranging from 15% to 1000%.

7. The composition according to claim 1, wherein the composition forms a film that has a Young's modulus ranging from 1 to 1000 MPa.

8. The composition according to claim 7, wherein the composition forms a film that has a Young's modulus ranging from 2 to 800 MPa.

9. The composition according to claim 1, wherein the composition forms a film that has an instantaneous elastic recovery $\epsilon_i$ greater than or equal to 25%.

10. The composition according to claim 9, wherein the composition forms a film that has an instantaneous elastic recovery $\epsilon_i$ greater than or equal to 35%.

11. The composition according to claim 10, wherein the composition forms a film that has an instantaneous elastic recovery $\epsilon_i$ ranging from 10% to 100%.

12. The composition according to claim 11, wherein the composition forms a film that has an instantaneous elastic recovery $\epsilon_i$ ranging from 25% to 98%.

13. The composition according to claim 12, wherein the composition forms a film that has an instantaneous elastic recovery $\epsilon_i$ ranging from 35% to 95%.

14. The composition according to claim 1, wherein the weight-average molecular weight of the film-forming gradient copolymer ranges from 5,000 g/mol to 1,000,000 g/mol.

15. The composition according to claim 14, wherein the weight-average molecular weight of the film-forming gradient copolymer ranges from 5,500 g/mol to 800,000 g/mol.

16. The composition according to claim 15, wherein the weight-average molecular weight of the film-forming gradient copolymer ranges from 6,000 g/mol to 500,000 g/mol.

17. The composition according to claim 1, wherein the number-average molecular weight of the film-forming gradient copolymer ranges from 5,000 g/mol to 1,000,000 g/mol.

18. The composition according to claim 17, wherein the number-average molecular weight of the film-forming gradient copolymer ranges from 5,500 g/mol to 800,000 g/mol.

19. The composition according to claim 18, wherein the number-average molecular weight of the film-forming gradient copolymer ranges from 6,000 g/mol to 500,000 g/mol.

20. The composition according to claim 1, wherein the film-forming gradient copolymer is such that on a curve of liquid adsorption chromatography ("LAC"), which shows the proportion of polymers as a function of the elution volume, the difference ($V^{1/2}max-V^{1/2}min$) is less than or equal to 3.5, wherein "$V^{1/2}min$" is the minimum value of the elution volume at mid-height of the curve, and "$V^{1/2}max$" is the maximum value of the elution volume at mid-height of the curve.

21. The composition according to claim 20, wherein the difference ($V^{1/2}\text{max}-V^{1/2}\text{min}$) ranges from 1 to 2.8.

22. The composition according to claim 21, wherein the difference ($V^{1/2}\text{max}-V^{1/2}\text{min}$) ranges from 1.2 to 2.5.

23. The composition according to claim 1, wherein the film-forming gradient copolymer is present in an amount ranging from 0.1% to 60% by weight, relative to the total weight of the composition.

24. The composition according to claim 23, wherein the film-forming gradient copolymer is present in an amount ranging from 0.5% to 40% by weight, relative to the total weight of the composition.

25. The composition according to claim 24, wherein the film-forming gradient copolymer is present in an amount ranging from 1% to 35% by weight, relative to the total weight of the composition.

26. The composition according to claim 25, wherein the film-forming gradient copolymer is present in an amount ranging from 5% to 30% by weight, relative to the total weight of the composition.

27. The composition according to claim 1, wherein the film-forming gradient copolymer is present in dissolved form or else in the form of an aqueous or organic dispersion.

28. The composition according to claim 27, wherein the dissolved form is present in water or an organic solvent.

29. The composition according to claim 1, comprising at least one additional constituent chosen from water; organic solvents; anionic, cationic, nonionic and amphoteric film-forming polymers; fixing polymers; volatile and non-volatile silicones; anionic, cationic, amphoteric and nonionic surfactants, thickening agents, pearlescent agents, UV filters, free-radical scavengers, perfumes, preservatives, pigments and colorants, pH adjusters, solubilizing agents, plasticizers, antifoaming agents, waxes and oils, vitamins, conditioning agents and organic and mineral particles, synthetic particles and particles of natural origin.

30. The composition according to claim 1, said composition being a haircare product for maintaining a hairstyle or for shaping the hair chosen from shampoos, gels, setting lotions, lotions for blow-drying, and fixing and styling compositions.

31. The composition according to claim 30, wherein the styling compositions are chosen from lacquers and sprays.

* * * * *